US011260195B2

(12) United States Patent
Kuzelka et al.

(10) Patent No.: US 11,260,195 B2
(45) Date of Patent: Mar. 1, 2022

(54) SYSTEMS AND METHODS FOR AN INDUCTIVELY HEATED ANESTHETIC VAPORIZER

(71) Applicant: General Electric Company, Schenectady, NY (US)

(72) Inventors: Russell James Kuzelka, McFarland, WI (US); Joseph James Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 745 days.

(21) Appl. No.: 16/137,462

(22) Filed: Sep. 20, 2018

(65) Prior Publication Data

US 2020/0094009 A1 Mar. 26, 2020

(51) Int. Cl.
| *A61M 16/10* | (2006.01) |
| *A61M 16/14* | (2006.01) |
| *A61M 16/20* | (2006.01) |
| *A61M 16/00* | (2006.01) |
| *A61M 16/18* | (2006.01) |

(52) U.S. Cl.
CPC ........ *A61M 16/109* (2014.02); *A61M 16/024* (2017.08); *A61M 16/142* (2014.02); *A61M 16/18* (2013.01); *A61M 16/203* (2014.02); *A61M 2016/0027* (2013.01); *A61M 2016/0033* (2013.01); *A61M 2205/3313* (2013.01); *A61M 2205/3327* (2013.01); *A61M 2205/3368* (2013.01); *A61M 2205/3375* (2013.01); *A61M 2205/3389* (2013.01); *A61M 2205/3653* (2013.01); *A61M 2205/52* (2013.01)

(58) Field of Classification Search
CPC .... A61M 16/00; A61M 16/01; A61M 16/022; A61M 16/024; A61M 16/104; A61M 16/1075; A61M 16/109; A61M 16/142; A61M 16/18; A61M 16/203; A61M 2016/1035
See application file for complete search history.

(56) References Cited

U.S. PATENT DOCUMENTS

| 5,243,973 A | * | 9/1993 | Falb | ...... A61M 16/18 128/203.12 |
| 6,951,628 B2 | | 10/2005 | Eidam et al. | |
| 2003/0051728 A1 | | 3/2003 | Lloyd | |
| 2006/0207593 A1 | * | 9/2006 | Dittmann | ...... A61M 16/104 128/203.12 |

(Continued)

FOREIGN PATENT DOCUMENTS

| GB | 2255912 A | * 11/1992 | ........... A61M 16/18 |
| GB | 2255912 A | 11/1992 | |

OTHER PUBLICATIONS

PCT application PCT/US2019/051435 filed Sep. 17, 2019; International Search Report/Written Opinion dated Dec. 12, 2019; 16 pages.

*Primary Examiner* — Joseph D. Boecker
(74) *Attorney, Agent, or Firm* — McCoy Russell LLP

(57) ABSTRACT

Methods and systems are provided for delivering anesthetic agent to a patient. In one embodiment, an anesthetic vaporizer includes a vaporizing chamber configured to hold a liquid anesthetic agent; a grid disposed within the vaporizing chamber; and a heating element positioned relative to the vaporizing chamber and configured to increase the temperature of the grid.

19 Claims, 11 Drawing Sheets

(56) References Cited

U.S. PATENT DOCUMENTS

| | | | |
|---|---|---|---|
| 2013/0220314 A1* | 8/2013 | Bottom | A61M 16/0891 128/200.14 |
| 2015/0128967 A1* | 5/2015 | Robinson | A24F 40/50 131/328 |
| 2016/0331913 A1* | 11/2016 | Bourque | A61M 11/042 |

* cited by examiner

SYSTEMS AND METHODS FOR AN INDUCTIVELY HEATED ANESTHETIC VAPORIZER

FIELD

Embodiments of the subject matter disclosed herein relate to anesthesia systems, and more particularly, to anesthetic vaporizers.

BACKGROUND

During some medical procedures, such as surgical procedures, a patient may be placed under general anesthesia by administrating an anesthetic agent. In some examples, the anesthetic agent may be a volatile anesthetic agent that is administered to the patient via an anesthetic vaporizer. For example, the anesthetic vaporizer may induce and control vaporization of the volatile anesthetic agent from a liquid form. A carrier gas (e.g., a mixture of oxygen and fresh air) may flow into the vaporizer and blend (e.g., mix and converge) with the anesthetic agent vapors generated by the vaporizer. An amount of carrier gas flowing into the vaporizer may be adjusted by an operator of the vaporizer (e.g., an anesthesiologist) in order to adjust a ratio of carrier gas to anesthetic agents within the vaporizer. The mixed gases may then flow to the patient, where they may be introduced via inhalation, for example. The concentration of the anesthetic agent in the mixed gases may be controlled to ensure sufficient anesthetic agent is provided for patient comfort without compromising patient safety.

BRIEF DESCRIPTION

In one embodiment, a system for an anesthesia vaporizer includes a vaporizing chamber configured to hold a liquid anesthetic agent, a grid disposed within the vaporizing chamber, and a heating element positioned relative to the vaporizing chamber and configured to increase the temperature of the grid. In this way, an anesthesia vaporizer is provided that may accurately deliver anesthetic agent to a patient with a fast response time and stability at both low fresh gas flow rates (<1 LPM) and high fresh gas flow rates (i.e., between 10 LPM and 15 LPM) without suffering a droop in output concentration.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 4A-4B are shown approximately to scale

DETAILED DESCRIPTION

Figure 1A:
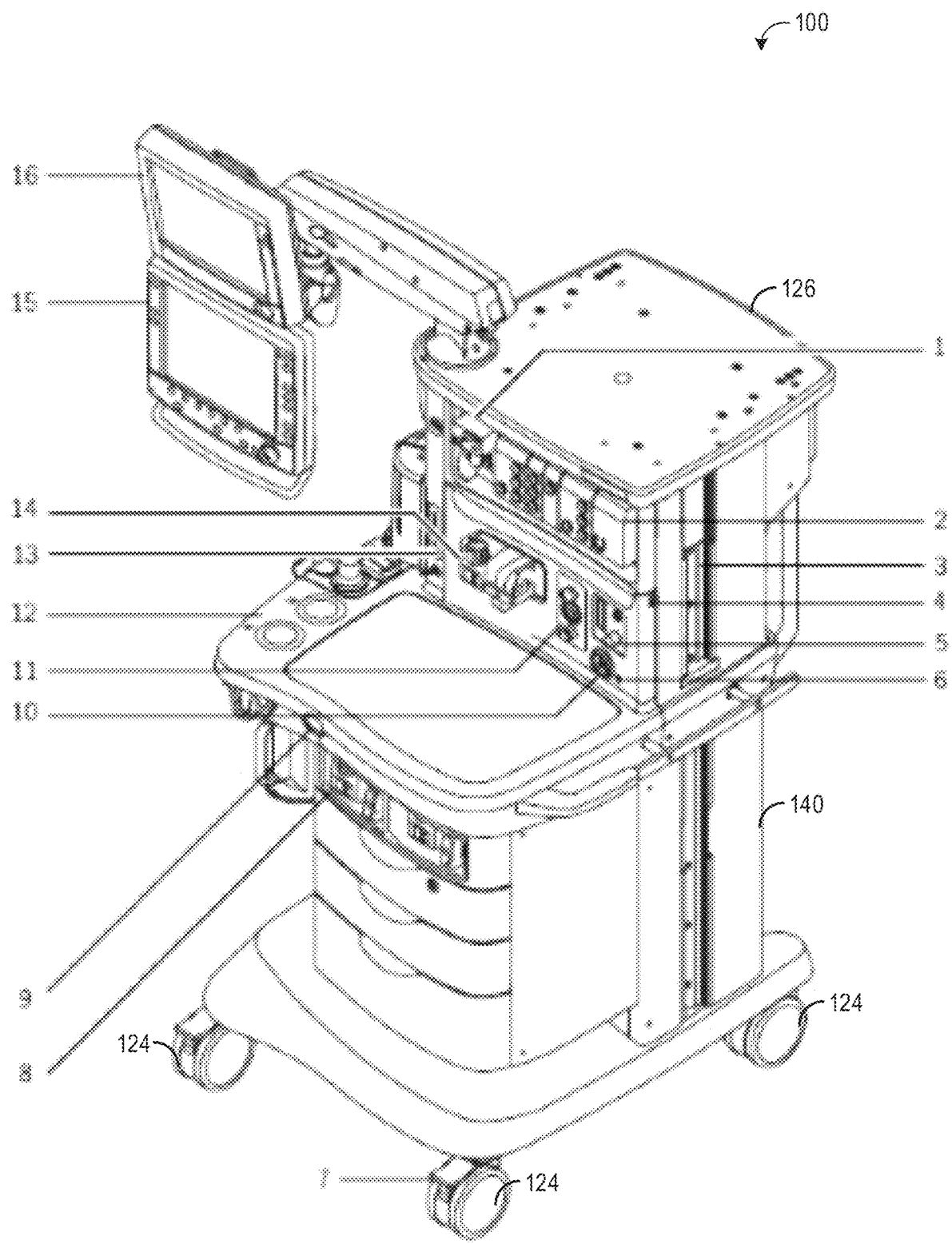
FIGS. 1A, 1B, and 1C show a first front perspective view, a second front perspective view, and back perspective view, respectively, of an anesthesia machine.

The following description relates to various embodiments of an anesthetic vaporizer system, which may be included in an anesthesia system. Fast, accurate, energy-efficient delivery of an anesthetic agent by an anesthetic vaporizer system may be challenging. For example, traditional anesthetic vaporizers systems may include pumps, compressors, pressurized sumps, pressurized secondary chambers, and/or injectors. As an example, a pump may deliver liquid anesthetic agent from a sump to a secondary chamber, where the liquid anesthetic agent is bulk boiled by a heater to vaporize the anesthetic agent and pressurize the secondary chamber. However, bulk boiling the liquid anesthetic agent increases an amount of energy consumed by the anesthetic vaporizer system due to the bulk thermal mass of the liquid anesthetic agent, which also creates a slow response to varying the vaporizer's temperature. In another example, a wick is used (cotton or plastic), where liquid anesthetic agent is absorbed by the wick and medical gas is passed over the wick surface. Agent is evaporated off from the wick and entrained in the gas stream. These systems are common and all suffer from slow response and droop, which is the inability to maintain high agent delivery rates in combination with high medical gas flow rates.

Thus, according to embodiments disclosed herein, an inductively heated grid may be disposed within a vaporizing chamber of an anesthetic vaporizer system in order to vaporize liquid anesthetic agent housed with the vaporizing chamber. In some embodiments, gas (e.g., oxygen and fresh air) may be bubbled through the inductively heated grid, but in other embodiments, gas may not be bubbled through the inductively heated grid. Further, according to embodiments disclosed herein, the amount of anesthetic agent vapor output by the anesthetic vaporizer system may be controlled in a closed-loop fashion based on electronic feedback signals to accurately provide a desired amount of anesthesia to a patient.

The embodiments disclosed herein may provide several advantages. For example, the embodiments disclosed herein may provide a quick response time compared with bulk boiling due to a smaller thermal mass of the inductively heated grid and the inductive heating (e.g., versus conductive heating). Further, by bubbling gas through the inductively heated grid, a temperature of the gas bubbles may be increased, thereby increasing an amount of anesthetic agent vaporized inside of each gas bubble and decreasing variability. Further still, the inductively heated grid may be configured to produce homogenous gas bubbles of an optimal size, thereby further increasing vaporization efficiency and further reducing variability in the amount of vaporized anesthetic agent produced. Additionally, high concentrations of anesthetic agent at high flow rates may be maintained.

Further still, the embodiments disclosed herein may provide additional advantages for controlling the amount of anesthetic agent vapor output by the anesthetic vaporizer system and delivered to the patient. For example, one or more flow control valves may be adjusted to adjust the amount of anesthetic agent vapor output by the anesthetic vaporizer system, providing control flexibility and allowing the amount of anesthetic agent vapor output by the anesthetic vaporizer system to be fine-tuned. Additionally, the heating of the inductively heated grid may be controlled separately from the amount of anesthetic agent vapor output by the anesthetic vaporizer system, thereby simplifying the control schemes.

Figure 1B:
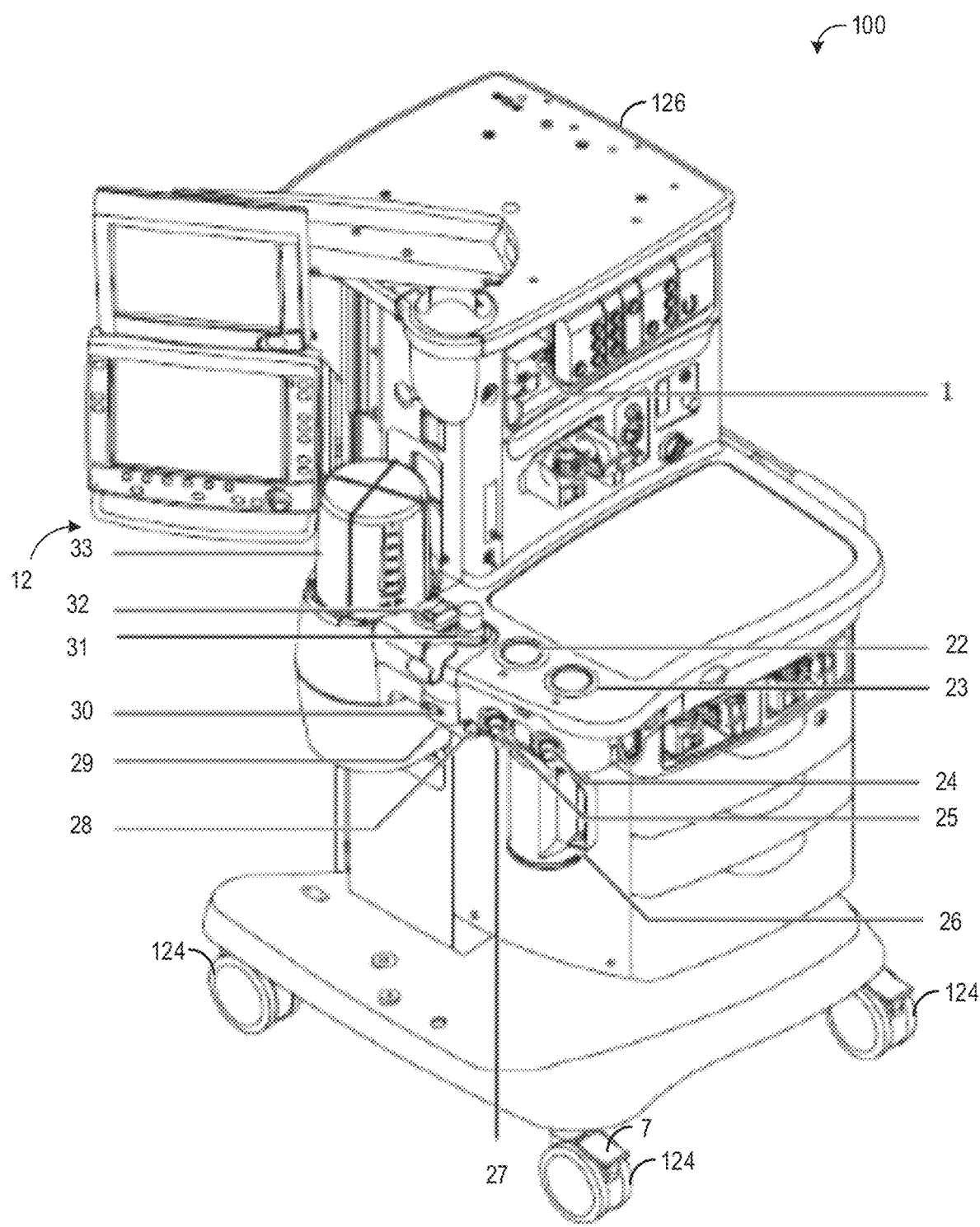
Figure 1C:
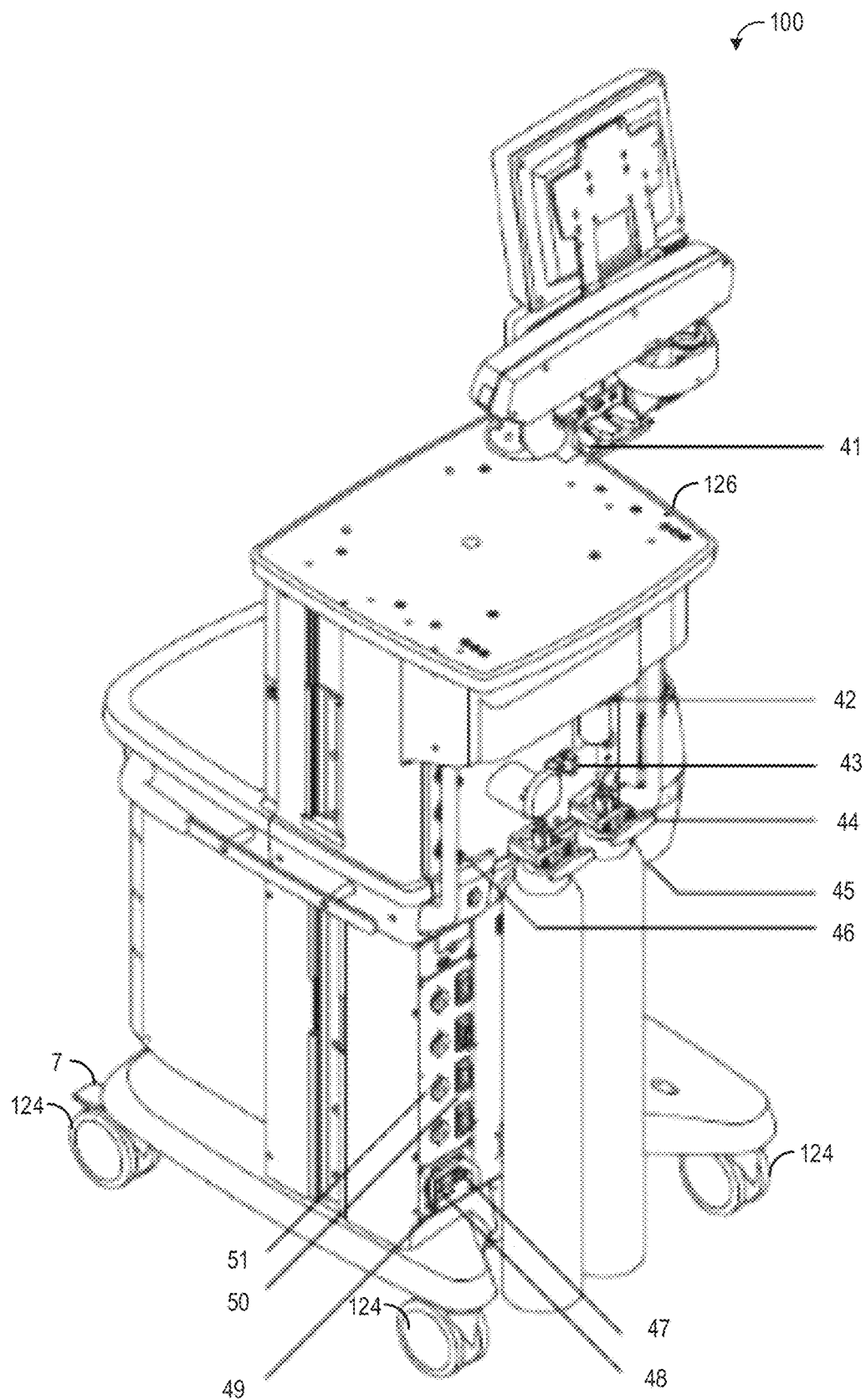
Figure 2:
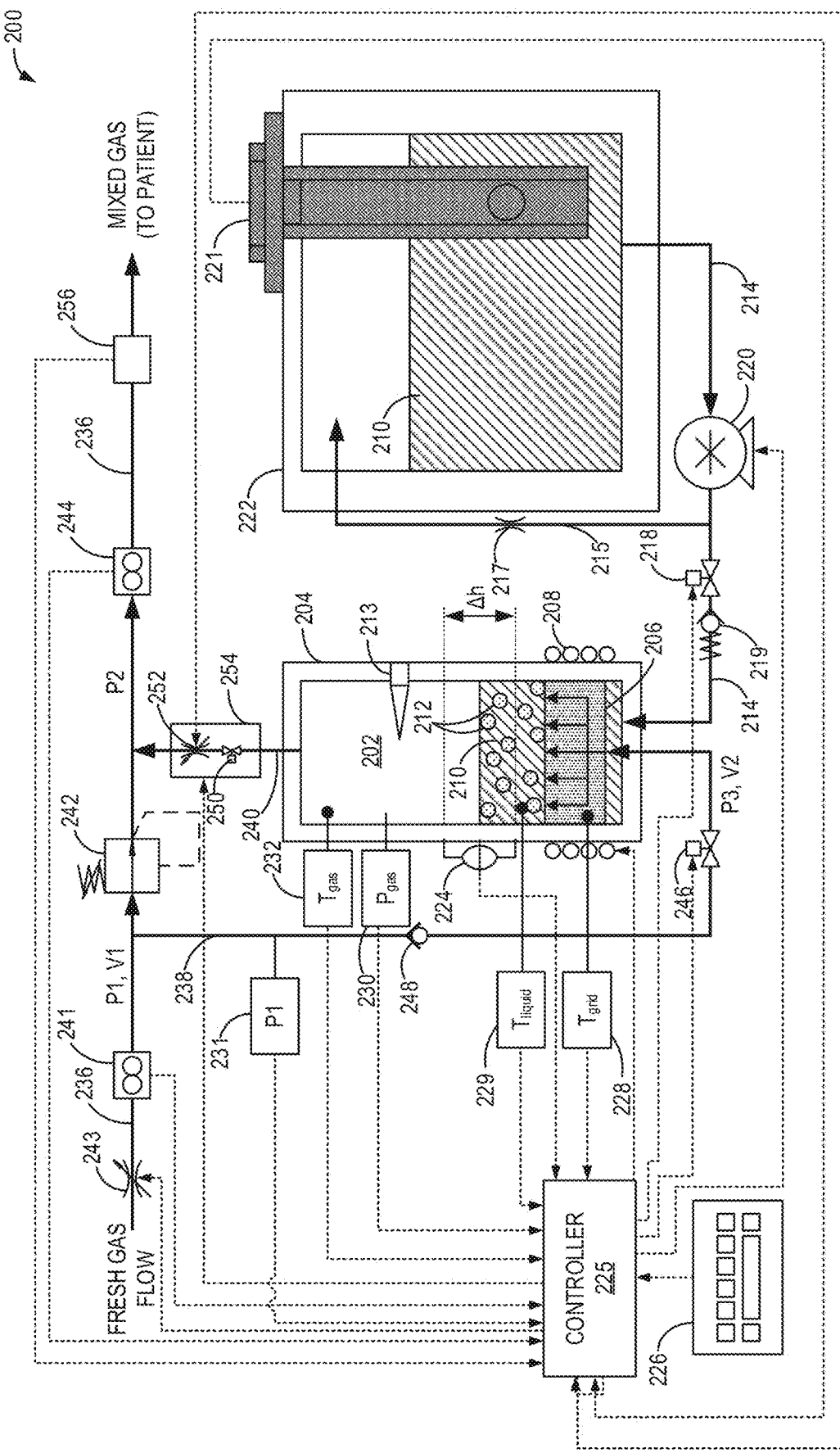
FIG. 2 schematically shows a first exemplary embodiment of an anesthetic vaporizer system.
Figure 3:
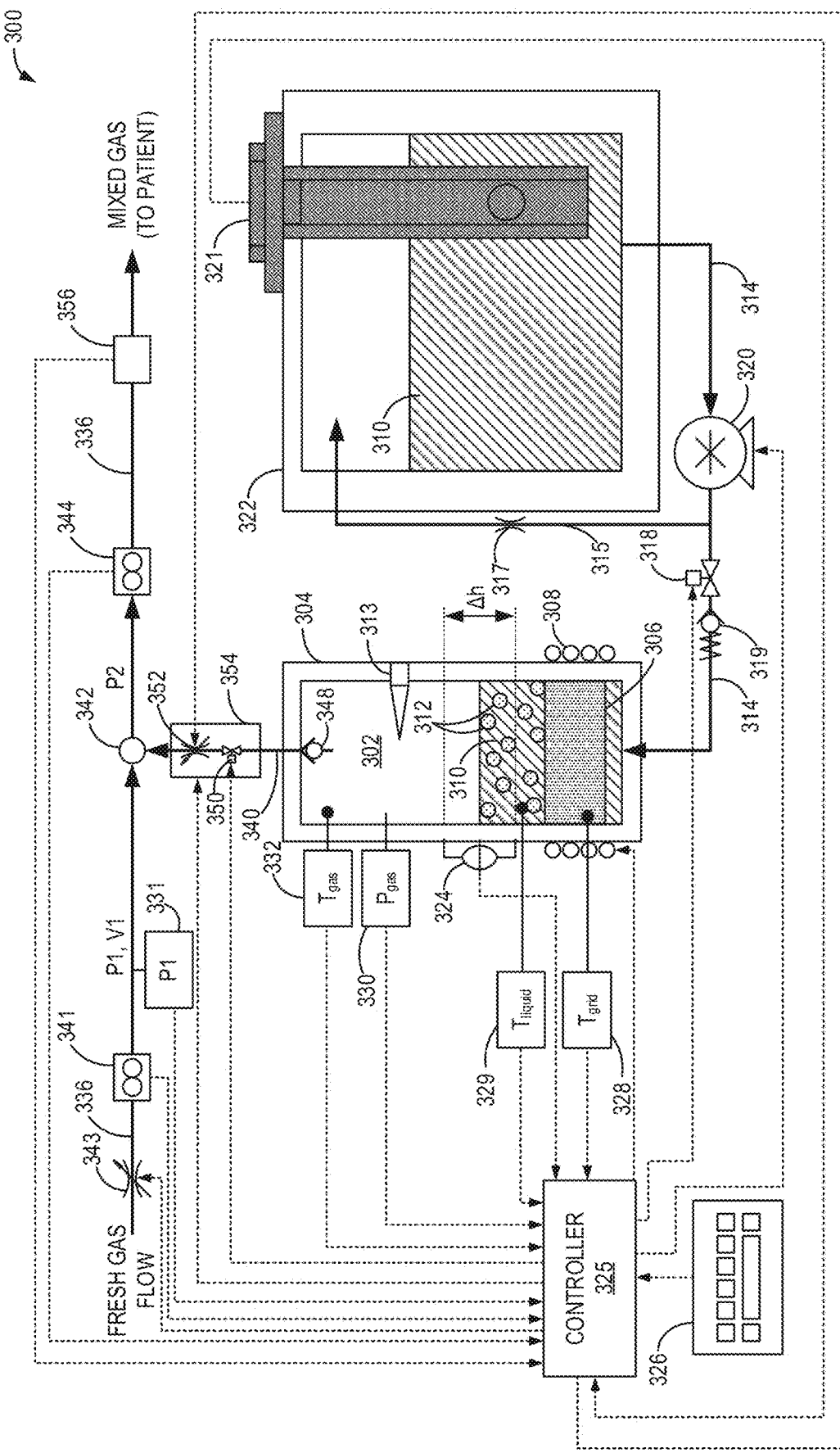
FIG. 3 schematically shows a second exemplary embodiment of an anesthetic vaporizer system.
Figure 4A:
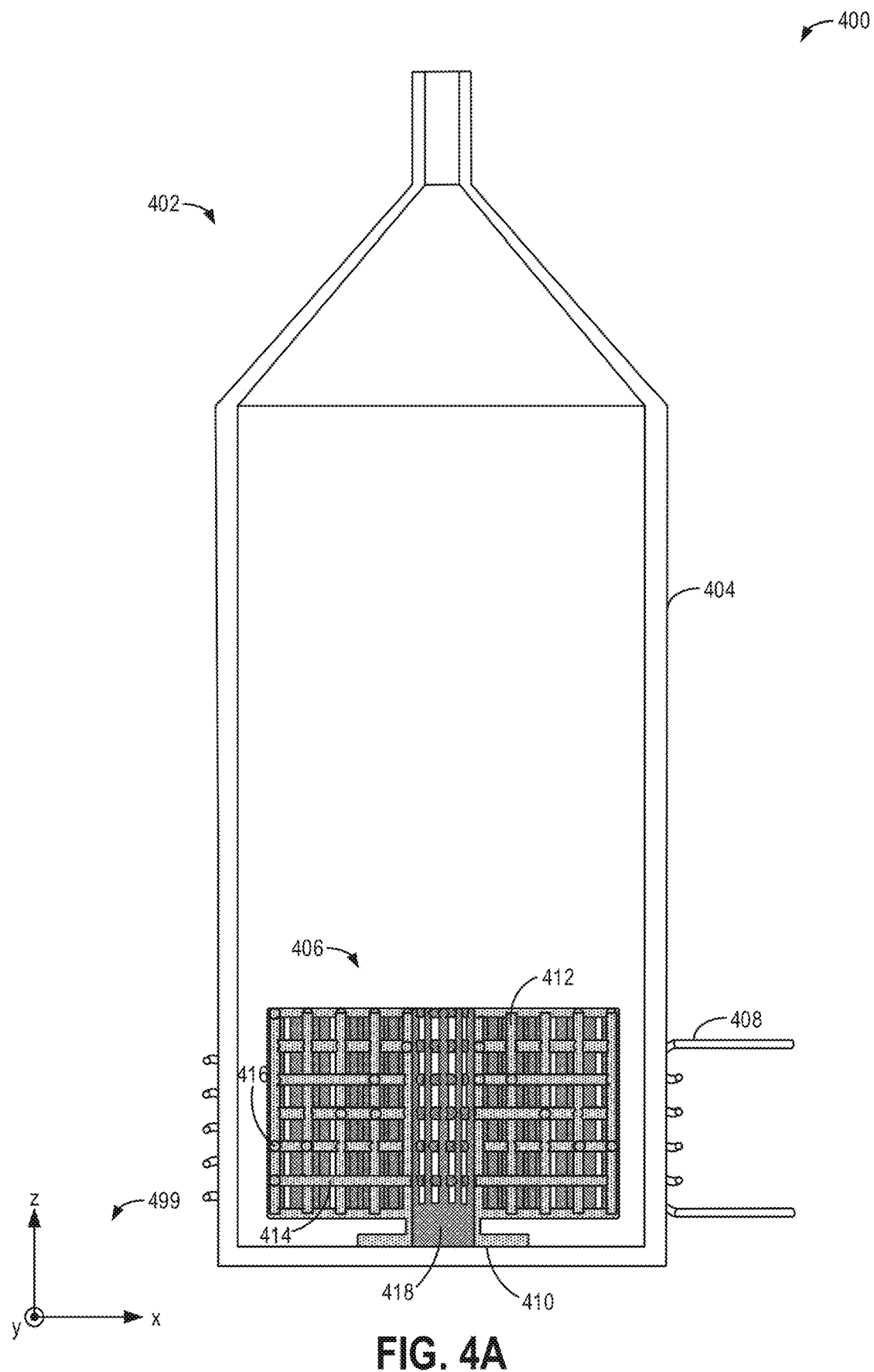
FIG. 4A shows a first cross-sectional view of an inductively heated grid housed within a vaporizing chamber.
Figure 4B:
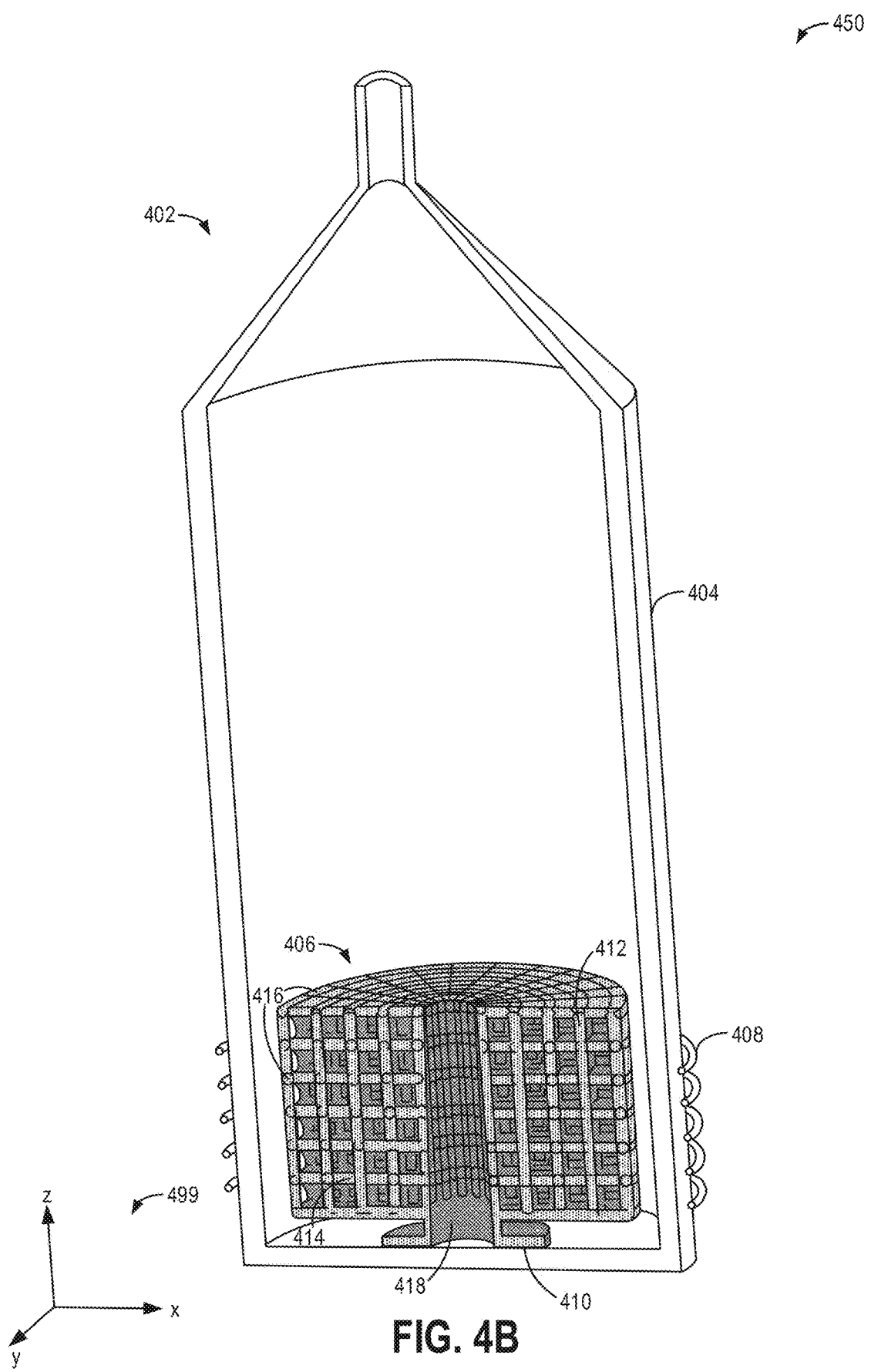
FIG. 4B shows a second cross-sectional view of the inductively heated grid housed within the vaporizing chamber.

FIGS. 1A-1C show views of an anesthesia machine according to an exemplary embodiment of the invention. FIG. 2 shows a first embodiment of an anesthetic vaporizer system, which may be included in the anesthesia machine of FIGS. 1A-1C. FIG. 3 shows a second embodiment of an anesthetic vaporizer system, which may be included in the anesthesia machine of FIGS. 1A-1C. FIGS. 4A and 4B show cross-sectional views of an inductively heated grid housed within a vaporizing chamber, which may be included in the anesthetic vaporizer systems of FIGS. 2 and 3 and manufactured according to the example method of FIG. 9. The grid may be heated using an example heater control loop shown in FIG. 6 and according to the example method of FIG. 8. The amount of vaporized anesthetic agent produced by the anesthetic agent system may be controlled using the example agent delivery control loop of FIG. 5 and according to the example method of FIG. 8.

FIGS. 1A-1C show an anesthesia machine 100 from a first side perspective view (FIG. 1A), a second side perspective view (FIG. 1B), and rear perspective view (FIG. 1C). FIGS. 1A-1C will be described collectively. Anesthesia machine 100 includes a frame 126 supported by casters 124, where the movement of the casters may be controlled (e.g., stopped) by one or more locks 7. In some examples, the frame 126 may be formed of a plastic material (e.g., polypropylene). In other examples, the frame 126 may be formed of a different type of material (e.g., metal, such as steel).

Anesthesia machine 100 also includes a respiratory gas module 1, one or more patient monitoring modules, such as a patient monitoring module 2, side rails 3, a light switch 4, an oxygen control 5, a main power indicator 6, an anesthetic agent storage bay 8, an oxygen flush button 9, a system activation switch 10 (which, in one example, permits gas flow when activated), an integrated suction 11, a ventilator 12 (explained in more detail below), an auxiliary oxygen flow control 13, an anesthetic vaporizer 14, an anesthesia display device 15, and a patient monitoring display device 16. Example embodiments of the anesthetic vaporizer will be described below with respect to FIG. 2 and FIG. 3. The anesthetic vaporizer 14 may vaporize the anesthetic agent and combine the vaporized anesthetic agent with one or more medical grade gases (e.g., oxygen, air, nitrous oxide, or combinations thereof), which may then be delivered to a patient.

A rear of the anesthesia machine 100 is shown in FIG. 1C. On the rear of the anesthesia machine, one or more pipeline connections 46 are present to facilitate coupling of the anesthesia machine to pipeline gas sources. Additionally, the rear of the anesthesia machine includes a cylinder yoke 44, via which one or more gas-holding cylinders may be coupled to the anesthesia machine. Thus, through the pipeline connection and/or cylinder connections, gas may be provided to the anesthesia machine, where the gas may include but is not limited to air, oxygen, and nitrous oxide. The gas that enters the anesthesia machine may mix with the vaporized anesthetic agent at the anesthetic vaporizer 14, as described above, and be supplied to a patient via the ventilator 12. The rear of the anesthesia machine may also include a serial port 41, a collection bottle connection 42, a cylinder wrench storage area 43, an anesthesia gas scavenging system 45, a main power inlet 47, a system circuit breaker 48, an equipotential stud 49, an outlet circuit breaker 50, and an isolated electrical outlet 51.

As shown in FIG. 1B, the ventilator 12 may include an expiratory check valve 22 at an expiratory port, an inspiratory check valve 23 at an inspiratory port, an inspiratory flow sensor 24, an expiratory flow sensor 25, an absorber canister 26, an absorber canister release 27, a leak test plug 28, a manual bag port 29, a ventilator release 30, an adjustable pressure-limiting valve 31, a bag/vent switch 32, and a bellows assembly 33. When a patient breathing circuit is coupled to the ventilator 12, breathing gases (e.g., air, oxygen, and/or nitrous oxide mixed with vaporized anesthetic agent) exit the machine from the inspiratory port (positioned at the same location as the inspiratory check valve 23) and travel to the patient. Expiratory gases from the patient re-enter the anesthesia machine via the expiratory port (positioned at the same location as the expiratory check valve 22), where carbon dioxide may be removed from the expiratory gases via the absorber canister 26.

During operation of the anesthetic vaporizer 14, an operator (e.g., an anesthesiologist) may adjust an amount of vaporized anesthetic agent that is supplied to the patient by adjusting a flow rate of gases from the gas source(s) (e.g., the gas pipelines) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of the anesthesia machine 100. In some embodiments, a first flow control valve may be positioned between the gas source(s) and the anesthetic vaporizer 14 and may be actuatable via the flow adjustment devices to a fully opened position, a fully closed position, and a plurality of positions between the fully opened position and the fully closed position. Different flow control valves that may be adjusted to vary an amount of vaporized anesthetic agent that is supplied to the patient will be further described below with respect to FIG. 2.

The anesthesia machine may additionally include one or more valves configured to bypass gases from the gas source(s) around the anesthetic vaporizer 14. The valves may enable a first portion of gases to flow directly from the gas source to the inspiratory port and a second portion of gases to flow from the gas source through the anesthetic vaporizer 14 to mix with the vaporized anesthetic agents prior to flowing to the inspiratory port. By adjusting a ratio of the first portion of gases relative to the second portion of gases, the operator may control a concentration of vaporized anesthetic agent administered to the patient via the inspiratory port.

Further, the adjustments described above may be facilitated at least in part based on output from the respiratory gas module 1. The respiratory gas module 1 may be configured to measure various parameters of the gases exiting the vaporizer and/or being provided to the patient. For example, respiratory gas module 1 may measure the concentrations of carbon dioxide, nitrous oxide, and the anesthetic agent provided to the patient. Further, respiratory gas module 1 may measure respiration rate, minimum alveolar concentration, patient oxygen, and/or other parameters. The output from the respiratory gas module 1 may be displayed via a graphical user interface on a display device (e.g., anesthesia display device 15 and/or patient monitoring display device 16) and/or used by a controller to provide closed-loop feedback control of the amount of anesthesia provided to the patient.

Ventilator 12 may optionally be coupled to a breathing circuit (not shown) including a plurality of tubes (e.g., gas passages). The breathing circuit may be coupled between an airway of a patient (e.g., via a breathing mask positioned to enclose the mouth and/or nose of the patient or a tracheal intubation tube) and the inspiratory port. Gases (e.g., oxygen, or a mixture of oxygen and vaporized anesthetic agents from anesthetic vaporizer 14) may flow from the inspiratory port, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gases (without the anesthetic agent) may flow into the airway of the patent (e.g., through inhalation) via the inspiratory check valve 23. As an example, the inspiratory check valve 23 may open automatically (e.g., without input or adjustment by the operator) in response to inhalation by the patient and may close automatically in response to exhalation by the patient. Similarly, the expiratory check valve 22 may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 14, the ventilator 12, the respiratory gas module 1, the anesthesia display device 15, and the patient monitoring display device 16.

The controller receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port may be controlled via an input device (e.g., keyboard, touchscreen, etc.) coupled to the electronic controller of the anesthesia machine 100. The controller 140 may display operating parameters of the anesthesia machine 100 via anesthesia display device 15 and/or patient monitoring display device 16. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by inspiratory flow sensor 24, for example.

Controller 140 is shown in FIG. 1A for illustrative purposes, and it is to be understood that controller 140 may be located internally of anesthesia machine 100 and thus may not be visible externally on anesthesia machine 100. Additionally, controller 140 may include multiple devices/modules that may be distributed throughout anesthesia machine 100. As such, controller 140 may include a plurality of controllers at various locations within anesthesia machine 100 and/or external to anesthesia machine 100 that are communicatively coupled through wired and/or wireless connections.

Anesthetic vaporizers, such as anesthetic vaporizer 14 shown in FIG. 1A, may employ various methods to vaporize a liquid anesthetic agent. For example, the anesthetic vaporizer may use a flow-over method (in which a carrier gas flows over a top surface of a volatile liquid anesthetic agent), a bubble-through method (in which the carrier gas is bubbled up through the liquid anesthetic agent), or a gas/vapor blender (in which heat is used to vaporize the liquid anesthetic agent, and the vapors are injected into a fresh gas flow). When the anesthetic agent undergoes a phase change from liquid to vapor, it absorbs energy, known as latent heat of vaporization. Therefore, even flow-over and bubble-through vaporizers may utilize a temperature compensation mechanism, at least in some examples. In the example of bubble-through vaporizers, as a size of the bubble produced decreases, a surface area-to-volume ratio of the bubble increases, which aids vaporization of the liquid anesthetic agent. Current methods to break the carrier gas into small bubbles include agitation and splashing. However, such methods may be inefficient and may result in heterogeneous gas bubble sizes.

FIG. 2 shows a first example embodiment of an anesthetic vaporizer system 200, which may be included in an anesthesia system (e.g., anesthesia system 100 shown in FIGS. 1A-1C). As one example, anesthetic vaporizer system 200 may be anesthetic vaporizer 14 of FIG. 1A. In particular, anesthetic vaporizer system 200 is a bubble-through anesthetic vaporizer, including a vaporizing chamber 202 defined by a housing 204 with a grid 206 disposed therein. Grid 206 may be comprised of a structurally defined three-dimensional metal mesh, as will be further described with respect to FIGS. 4A-4B. For example, grid 206 may be 3D-printed to a defined geometry, thereby reducing part-to-part variation.

A heating element 208 is positioned external to vaporizing chamber 202, such as in direct contact with (e.g., touching) a lower portion of housing 204. In other embodiments, heating element 208 may not be in direct contact with housing 204. In still further examples, heating element 208 may be positioned in an interior of vaporizing chamber 202 and/or integrated at least partially within housing 204. Heating element 208 may heat through induction, such as where heating element 208 is an inductive heating coil. For example, heating element 208 may selectively heat grid 206 via induction without becoming hot itself and/or without directly heating additional components of anesthetic vaporizer system 200 (e.g., housing 204). However, in some embodiments, heating element 208 may heat through conduction.

A lower portion of vaporizing chamber 202 is shown holding a liquid anesthetic agent 210 that is supplied from a sump 222 via a conduit 214 and a pump 220. The liquid anesthetic agent 210 may be isoflurane, sevoflurane, or another liquid anesthetic agent of similar volatility, for example. Pump 220 may be a positive displacement pump, such as a reciprocating positive displacement pump, for example. Pump 220 may be selectively operated to deliver liquid anesthetic agent 210 from sump 222 to vaporizing chamber 202 in response to a command signal from a controller 225, as will be further described below. Controller 225 may be an electronic controller including a processor operatively connected to a memory. Controller 225 may be included in (e.g., a part of) or communicatively coupled to controller 140 shown in FIG. 1A, for example. Furthermore, pump 220 may decouple vaporizing chamber 202 from sump 222, enabling sump 222 to be refilled while anesthetic vaporizer system 200 is in use.

Conduit 214 may further include a shut-off valve 218 coupled between pump 220 and vaporizing chamber 202. For example, shut-off valve 218 may be an on-off valve, wherein shut-off valve 218 is actuated to an open (e.g., fully open) position that allows liquid anesthetic agent 210 to flow between sump 222 and pump 220 or a closed (e.g., fully closed) position that prevents (e.g., blocks) the flow of liquid anesthetic agent 210 between pump 220 and vaporizing chamber 202. Shut-off valve 218 may be actuated between the open and closed positions in response to a command signal from controller 225, for example. A liquid return line 215 may be coupled to conduit 214 between shut-off valve 218 and pump 220 to reduce pressure build up between shut-off valve 218 and pump 220, such as when shut-off valve 218 is closed. For example, excess liquid anesthetic agent 210 provided by pump 220 may be returned to sump 222 via liquid return line 215.

Conduit 214 may further include a check valve 219 coupled between shut-off valve 218 and vaporizing chamber 202. Check valve 219 may be a one-way, spring-loaded check valve that allows liquid anesthetic agent 210 to flow from pump 220, through open shut-off valve 218, to vaporizing chamber 202 and prevents liquid anesthetic agent 210 from flowing from vaporizing chamber 202 to pump 220. For example, check valve 219 may open automatically (e.g., without input or adjustment from the controller or operator) to flow the liquid anesthetic agent 210 toward vaporizing chamber 202 and close automatically to prevent the liquid anesthetic agent 210 from flowing from vaporizing chamber 210 back to pump 220. Further, liquid return line 215 may include a restriction 217, such as an orifice, to control flow through liquid return line 215 such that liquid anesthetic agent 210 preferentially flows through check valve 219 instead of restriction 217 when shut-off valve 218 is open.

Controller 225 may selectively activate pump 220 to provide liquid anesthetic agent 210 from sump 222 to vaporizing chamber 202 responsive to a measurement received from a level sensor 224. For example, level sensor 224 may be an optical, ultrasonic, capacitive, float, or pressure-based level sensor configured to measure a level of liquid anesthetic agent 210 in vaporizing chamber 202. As one example, controller 225 may be configured to maintain the level of liquid anesthetic agent within a threshold range $\Delta h$. The threshold range $\Delta h$ may be defined by a first, lower threshold level and a second, higher threshold level. The first threshold level may be a pre-determined, non-zero level of the liquid anesthetic agent that is calibrated to maintain a minimum distance between grid 206 and a surface of the liquid anesthetic agent 210 for desired vaporization properties. The second threshold level may be a pre-determined, non-zero level of the liquid anesthetic agent that is calibrated to prevent overfilling of vaporizing chamber 202 with liquid anesthetic agent 210 and minimize variation in the desired vaporization properties throughout the threshold range. For example, controller 225 may activate pump 220 in response to the level of anesthetic agent 210 reaching the first, lower threshold level and deactivate pump 220 responsive to the level of anesthetic agent 210 reaching the second, higher threshold level. As another example, additionally or alternatively, controller 225 may activate pump 220 at a duty cycle selected based on the measured level of the liquid anesthetic agent and/or a rate of change of the measured liquid anesthetic agent level to maintain a consistent level of the liquid anesthetic agent 210 in vaporizing chamber 202. For example, the controller may input the measured level of the liquid anesthetic agent and/or the rate of change into one or more look-up tables, algorithms, or functions and output the selected duty cycle. Controller 225 may then activate pump 220 at the selected duty cycle, which may be adjusted as the measured level of the liquid anesthetic agent and/or the rate of change of the measured level changes. For example, as the measured level increases, the duty cycle of pump 220 activation may decrease, and as the measured level decreases, the duty cycle of pump 220 activation may increase. In addition, a positive displacement stepper motor pump may also be used, where each positive displacement step of the pump is equivalent to a specified volume of anesthetic liquid. In this manner, the pump can be used to precisely fill the vaporization chamber and prevent overfill by recording the number of pump steps delivered. This approach may also be used to record a volume of anesthetic agent delivered to the vaporization chamber, which may be valuable for vaporizer run-time/maintenance analysis (service metrics), liquid leak detection, precise determination of amount of liquid anesthetic remaining and available for delivery, vaporization efficiency calculations, etc. Further still, in some embodiments, a level switch 213 may be included to prevent overfilling of vaporizing chamber 202 with liquid anesthetic agent 210.

An upper portion of vaporizing chamber 202 (e.g., above a surface of liquid anesthetic 210) holds vapor, which may be a mixture of vaporized anesthetic agent and a carrier gas from a fresh gas flow. The fresh gas flow, and thus the carrier gas, may include one or more medical grade gases, such as oxygen, air, nitrous oxide, and combinations thereof. The fresh gas flow may be provided via one or more gas pipelines (e.g., via pipeline connections 46 shown in FIG. 1C) and/or one or more gas-holding cylinders (e.g., via cylinder yoke 44 of FIG. 1C). As shown in FIG. 2, the fresh gas flow may enter the anesthetic vaporizer system 200 via a first gas passage 236. A first proportional valve 243 coupled to the first gas passage 236 may be adjusted by controller 225 to control an amount (or flow rate) of fresh gas flowing through the first gas passage 236. First proportional valve 243 may be a variable valve, such a continuously variable valve, that may be adjusted by controller 225 between a plurality of positions ranging from a fully open to a fully closed position. For example, as a degree of opening of first proportional valve 243 increases, an amount (e.g., flow rate) of fresh gas flowing through first gas passage 236 may increase.

A first mass flow sensor 241 may be coupled to first gas passage 236 downstream of first proportional valve 243 to measure a flow rate of the fresh gas flow entering the anesthetic vaporizer system 200. For example, first mass flow sensor 241 may be an ultrasonic flow meter or a calorimetric (thermal) mass flow meter. A pressure regulator 242 coupled to first gas passage 236 may limit a pressure of the fresh gas downstream of pressure regulator 242. For example, pressure regulator 242 may be a pressure reducing valve such that a pressure of the fresh gas flow downstream of pressure regulator 242 does not exceed a pressure setpoint of the pressure regulator.

A second gas passage 238 branches off of the first gas passage between first flow sensor 241 and pressure reducing valve 242 to provide carrier gas (e.g., a portion of the fresh gas flow that flows to vaporizing chamber 202) to grid 206. For example, second gas passage 238 may pass through an opening in housing 204, which may include a gas-tight seal, to flow the carrier gas to grid 206. Further, pressure regulator 242 may control a gas pressure within second gas passage 238. Second gas passage 238 may include one or more valves disposed therein. As shown in FIG. 2, second gas passage 238 includes a check valve 248 and a shut-off valve 246. Check valve 248 may be a one-way valve that allows the carrier gas to flow from the fresh gas flow to grid 206 and prevents the carrier gas from flowing from grid 206 toward common gas passage 234. For example, check valve 248 may open automatically (e.g., without input or adjustment from a controller or operator) to flow the carrier gas toward grid 206 and close automatically to prevent gas flow toward common gas passage 234. In contrast, shut-off valve 246 may be an electronically or mechanically actuated valve that is operated responsive to input from controller 225 and/or an operator of anesthetic vaporizer system 200 (e.g., an anesthesiologist). For example, shut-off valve 246 may be an on-off valve, where shut-off valve 246 is actuated to an open (e.g., fully open) position that allows gas flow through shut-off valve 246 or a closed (e.g., fully closed) position that prevents (e.g., blocks) gas flow through shut-off valve 246 in response to an appropriate command signal from controller 225.

The carrier gas delivered via second gas passage 238 flows through grid 206, which is located near a bottom of vaporizing chamber 202 and is completely submerged within liquid anesthetic agent 210, to form a plurality of gas bubbles 212. The plurality of gas bubbles 212 pass through liquid anesthetic agent 210, becoming saturated with vaporized anesthetic agent, as they rise to the surface of the liquid. Grid 206 increases an interfacial area between the carrier gas and liquid anesthetic agent 210 by decreasing a size of the gas bubbles 212, which in turn increases a rate of vaporization of liquid anesthetic agent 210. For example, gas bubbles 212 may be fine and/or micro bubbles. A geometry of grid 206 may be selected to optimize an efficiency of the vaporization of the liquid anesthetic agent, which may be affected by the size of the gas bubbles 212 and the swirl of the gas bubbles 212, for example. For example, the size of the gas bubbles 212 may be selected to maximize the surface area of the fresh gas in contact with the liquid anesthetic agent 210 while reducing back pressure (e.g., a pressure drop across grid 206) and to generate a defined and homogenous gas distribution. As an example, the large surface area-to-volume ratio of each small gas bubble 212 enables each gas bubble to become fully saturated with vapor of the liquid anesthetic agent 210. In addition to the bubble size, vaporization of the liquid anesthetic agent is affected by an amount of time the gas bubbles 212 spend in the liquid anesthetic agent 210 (which may be controlled for by controlling the level of the liquid anesthetic agent 210 in vaporizing chamber 202, as described above) and a temperature difference between the gas bubbles 212 and the liquid anesthetic agent 210. By activating heating element 208 to heat grid 206, the latent heat of vaporization for the phase transition from the liquid form of the anesthetic agent to the vapor form may be provided via direct contact with the heated grid 206 while each gas bubble 212 is evolved. As an example, when a desired anesthetic agent flow rate (or concentration) is low, an amount of power provided to heating element 208 may be lower, preventing cool off from the latent heat of vaporization without increasing a temperature of the gas bubbles 212 and/or the liquid anesthetic agent 210. As another example, when a desired anesthetic agent flow rate (or concentration) is high, the amount of power provided to heating element 208 may be higher to facilitate production of additional vapor bubbles, such as through nucleated boiling off of the surface of grid 206. Thus, all of the carrier gas that flows through vaporizing chamber 202 via the heated grid 206 may be fully saturated with vapor from liquid anesthetic agent 210, even at high fresh gas flow rates (e.g., 10 L/min).

Vapor, such as the carrier gas that is saturated with vaporized anesthetic agent, may flow out of vaporizing chamber 202 via a third gas passage 240 (e.g., a vapor delivery passage). For example, third gas passage 240 may pass through an opening at or near a top of housing 204 and form a junction with first gas passage 236 to fluidically couple the upper portion of vaporizing chamber 202 with first gas passage 236. Third gas passage 240 is shown including a shut-off valve 250 and a second proportional valve 252 within a manifold heater 254. Shut-off valve 250 may be an electronically or mechanically actuated valve that is adjusted responsive to input from controller 225 and/or the operator. For example, shut-off valve 250 may be an on-off valve, wherein shut-off valve 250 is actuated to an open (e.g., fully open) position that allows gas flow through shut-off valve 250 or a closed (e.g., fully closed) position that prevents (e.g., blocks) gas flow through shut-off valve 250 in response to an appropriate command signal from controller 225. Shut-off valve 250 may be closed to quickly stop the supply of the anesthetic agent to a patient, for example. Second proportional valve 252 may be a variable valve, such a continuously variable valve, that may be adjusted by controller 225 between a plurality of positions ranging from a fully open to a fully closed position. For example, as a degree of opening of second proportional valve 252 increases, an amount (e.g., flow rate) of vapor flowing from vaporizing chamber 202 to first gas passage 236 (e.g., via third gas passage 240) may increase. Conversely, as the degree of opening of second proportional valve 252 decreases, the amount of vapor delivered from vaporizing chamber 202 to first gas passage 236 may decrease. Manifold heater 254 may heat shut-off valve 250 and second proportional valve 252 to prevent condensation of the vaporized anesthetic agent in the valves. As a non-limiting example, manifold heater 254 may be operated to maintain shut-off valve 250 and second proportional valve 252 at a substantially constant temperature, such as 40° C.

Upstream of the junction with third gas passage 240, first gas passage 236 carries a portion of the fresh gas flow called bypass gas. The bypass gas does not pass through vaporizing chamber 202. An amount of bypass gas flowing through first gas passage 236 may be adjusted by adjusting the fresh gas flow and may be limited by pressure regulator 242. The bypass gas, containing no vaporized anesthetic agent, and the vapor from vaporizing chamber 202, containing the carrier gas saturated with the vaporized anesthetic agent, mix at and downstream of the junction between first gas passage 236 and third gas passage 240. The mixed gas may then be delivered to the patient via an inspiratory limb of a breathing circuit (e.g., via the inspiratory port described with respect to FIG. 1B). A second mass flow sensor 244 may be coupled to first gas passage 236 downstream of the junction with third gas passage 240 to measure a flow rate of the mixed gas exiting the anesthetic vaporizer system 200. For example, second mass flow sensor 244 may be an ultrasonic flow meter or a calorimetric (thermal) mass flow meter. In the case of an ultrasonic flow metering architecture, the output anesthetic agent concentration may be calculated by the difference in the measured time of flight (TOF) between upstream ultrasonic flow sensor 241 and downstream ultrasonic flow sensor 244. Further, an independent concentration sensor 256 may be coupled to first gas passage 236 downstream of the junction with third gas passage 240. Concentration sensor 256 may be any suitable sensor that is configured to measure a concentration of the anesthetic agent in the mixed gas. In one example, concentration sensor 256 may be an optical sensor that transmits light of a suitable wavelength (e.g., infrared) through the mixed gas and determines a concentration of the anesthetic agent based on an absorption of the light by the mixed gas. In other examples, the concentration sensor may be a carbon dioxide or oxygen sensor that measures the concentration of the anesthetic agent based on a displacement of the carbon dioxide or oxygen relative to a supplied concentration of carbon dioxide or oxygen in the fresh gas flow. Concentration sensor 256 may output a signal to controller 225 indicative of the measured concentration of the anesthetic agent (e.g., the concentration of the anesthetic agent vapor) in the mixed gas.

In addition to receiving signals output by level sensor 224, concentration sensor 256, first mass flow sensor 241, and second mass flow sensor 224, controller 225 may receive additional signals, including a measured level of liquid anesthetic agent 210 within sump 222 from a level sensor 221, which may be an infrared level sensor, for example; a measured vapor pressure inside vaporizing chamber 202 ($P_{gas}$) from a pressure sensor 230 coupled to an upper portion of vaporizing chamber 202; a measured fresh gas flow pressure (P1) from a pressure sensor coupled to second gas passage 238 upstream of check valve 248; a measured vapor temperature inside vaporizing chamber 202 ($T_{gas}$) from a temperature sensor 232 coupled to an upper portion of vaporizing chamber 202; a measured temperature of grid 206 ($T_{grid}$) from a temperature sensor 228 coupled to grid 206; and a measured temperature of liquid anesthetic agent 210 ($T_{liquid}$) from a temperature sensor 229 that is immersed in the liquid anesthetic agent. Controller 225 receives the signals from the various sensors of FIG. 2, processes the input data, and employs the various actuators of FIG. 2 to adjust operation of anesthetic vaporizer system 200 based on the received signals and instructions stored on a memory of the controller. For example, controller 225 may receive the measured concentration of the anesthetic agent from concentration sensor 256 and adjust a position of one or more of the first proportional valve 243 and the second proportional valve 252, as described further below with respect to FIG. 7. As another example, controller 225 may receive $T_{grid}$ from temperature sensor 228, $T_{liquid}$ from temperature sensor 229 and a current or voltage supplied to heating element 208 based on the input measurements, as further described below with respect to FIG. 8.

Further, data may be input to controller 225 by the operator of anesthetic vaporizer system 200 via a user input device 226 that is operationally connected to the controller and thus configured to transmit an input signal to controller 225 (e.g., via wired or wireless communication). User input device 226 may include one or more of a mouse, a keyboard, a voice input device, a touch input device for receiving a gesture from the operator, a motion input device for detecting non-touch gestures and other motions by the operator, and other comparable input devices, as well as associated processing elements capable of receiving user input from the operator.

Further still, controller 225 may calculate a concentration of the anesthetic agent output by anesthetic vaporizer system 200 and delivered to the patient according to the equation:

$$\% \text{ Agent} = \frac{Fv\left(\frac{VPa}{Pb-VPa}\right)}{Ft \times 1000} \times 100$$

where % Agent is a percentage concentration of the anesthetic agent in the inspiratory limb of the breathing circuit, Fv is a measured flow of gas through the vaporizer (in mL/min, such as measured by second mass flow sensor 244), Ft is a total fresh gas flow into the vaporizer (in L/min, such as measured by first mass flow sensor 241), VPa is a vapor pressure of the volatile anesthetic agent (in mmHg), and Pb is barometric (e.g., ambient) pressure (in mmHg). The vapor pressure of the volatile anesthetic agent may be a known property of the anesthetic agent at a given temperature (e.g., as measured by temperature sensor 229) that is stored in a memory of the controller, for example, in a look-up table. As an example, the operator may input an indication of which anesthetic agent is currently housed in the vaporizing chamber 202 to the controller via the input device. Pb may be measured by an ambient pressure sensor or estimated. The calculated concentration may be used as a sanity check against the concentration of the anesthetic agent measured by concentration sensor 256, for example.

FIG. 3 shows a second example embodiment of an anesthetic vaporizer system 300, which may be included in an anesthesia system (e.g., anesthesia system 100 shown in FIGS. 1A-1C). As one example, anesthetic vaporizer system 300 may be anesthetic vaporizer 14 of FIG. 1A. In particular, anesthetic vaporizer system 300 is an inductively heated anesthetic vaporizer, including a vaporizing chamber 302 defined by a housing 304 with a grid 306 disposed therein. Grid 306 may be comprised of a structurally defined three-dimensional metal mesh, as will be further described with respect to FIGS. 4A-4B. For example, grid 306 may be the same as or different than grid 206 shown in FIG. 2. A heating element 308 is positioned external to vaporizing chamber 302, such as in direct contact with (e.g., touching) a lower portion of housing 304. In another example, heating element 308 may not be in direct contact with housing 304. Heating element 308 may heat through induction, such as where heating element 308 is an inductive heating coil. For example, heating element 308 may selectively heat grid 306 via induction without becoming hot itself and/or without directly heating additional components of anesthetic vaporizer system 300 (e.g., housing 304). However, in other examples, heating element 308 may heat through conduction.

A lower portion of vaporizing chamber 302 is shown holding a liquid anesthetic agent 310 that is supplied from a sump 322 via a conduit 314 and a pump 320. The liquid anesthetic agent 310 may be desflurane or another liquid anesthetic agent of similar volatility, for example. Pump 320 may be a positive displacement pump, such as a reciprocating positive displacement pump, for example. Pump 320 may be selectively operated to deliver liquid anesthetic agent 310 from sump 322 to vaporizing chamber 302 in response to a command signal from a controller 325, as will be further described below. Controller 325 may be an electronic controller including a processor operatively connected to a memory. Controller 325 may be included in (e.g., a part of) or communicatively coupled to controller 140 shown in FIG. 1A, for example. Furthermore, pump 320 may decouple vaporizing chamber 302 from sump 322, enabling sump 322 to be refilled while anesthetic vaporizer system 300 is in use.

Conduit 314 may further include a shut-off valve 318 coupled between pump 320 and vaporizing chamber 302. For example, shut-off valve 318 may be an on-off valve, wherein shut-off valve 318 is actuated to an open (e.g., fully open) position that allows liquid anesthetic agent 310 to flow between sump 322 and pump 320 or a closed (e.g., fully closed) position that prevents (e.g., blocks) the flow of liquid anesthetic agent 310 between pump 320 and vaporizing chamber 302. Shut-off valve 318 may be actuated between the open and closed positions in response to a command signal from controller 325, for example. A liquid return line 315 may be coupled to conduit 314 between shut-off valve 318 and pump 320 to reduce pressure build up between shut-off valve 318 and pump 320, such as when shut-off valve 318 is closed. For example, excess liquid anesthetic agent 310 provided by pump 320 may be returned to sump 322 via liquid return line 315.

Conduit 314 may further include a check valve 319 coupled between shut-off valve 318 and vaporizing chamber 302. Check valve 319 may be a one-way, spring-loaded check valve that allows liquid anesthetic agent 310 to flow from pump 320, through open shut-off valve 318, to vaporizing chamber 302 and prevents liquid anesthetic agent 310 from flowing from vaporizing chamber 302 to pump 320. For example, check valve 319 may open automatically (e.g., without input or adjustment from the controller or operator) to flow the liquid anesthetic agent 310 toward vaporizing chamber 302 and close automatically to prevent the liquid anesthetic agent 310 from flowing from vaporizing chamber 310 back to pump 320. Further, liquid return line 315 may include a restriction 317, such as an orifice, to control flow through liquid return line 315 such that liquid anesthetic agent 310 preferentially flows through check valve 319 instead of restriction 317 when shut-off valve 318 is open.

Controller 325 may selectively activate pump 320 to provide liquid anesthetic agent 310 from sump 322 to vaporizing chamber 302 responsive to a measurement received from a level sensor 324. For example, level sensor 324 may be an optical, capacitive, ultrasonic, float or pressure-based level sensor configured to measure a level of liquid anesthetic agent 310 in vaporizing chamber 302. As one example, controller 325 may be configured to maintain the level of liquid anesthetic agent within a threshold range $\Delta h$. The threshold range $\Delta h$ may be defined by a first, lower threshold level and a second, higher threshold level. The first threshold level may be a pre-determined, non-zero level of the liquid anesthetic agent that is calibrated to maintain a minimum distance between grid 306 and a surface of the liquid anesthetic agent 310 for desired vaporization properties. The second threshold level may be a pre-determined, non-zero level of the liquid anesthetic agent that is calibrated to prevent overfilling of vaporizing chamber 302 with liquid anesthetic agent 310 and minimize variation in the desired vaporization properties throughout the threshold range. For example, controller 325 may activate pump 320 in response to the level of anesthetic agent 310 reaching the first, lower threshold level and deactivate pump 320 responsive to the level of anesthetic agent 310 reaching the second, higher threshold level. As another example, additionally or alternatively, controller 325 may activate pump 320 at a duty cycle selected based on the measured level of the liquid anesthetic agent and/or a rate of change of the measured liquid anesthetic agent level to maintain a consistent level of the liquid anesthetic agent 310 in vaporizing chamber 302. For example, the controller may input the measured level of the liquid anesthetic agent and/or the rate of change into one or more look-up tables, algorithms, or functions and output the selected duty cycle. Controller 325 may then activate pump 320 at the selected duty cycle, which may be adjusted as the measured level of the liquid anesthetic agent and/or the rate of change of the measured level changes. For example, as the measured level increases, the duty cycle of pump 320 activation may decrease, and as the measured level decreases, the duty cycle of pump 320 activation may increase. In addition, a positive displacement stepper motor pump may also be used, where each positive displacement step of the pump is equivalent to a specified volume of anesthetic liquid. In this manner, the pump can be used to precisely fill the vaporization chamber and prevent overfill by recording the number of pump steps delivered. This approach may also be used to record a volume of anesthetic agent delivered to the vaporization chamber, which may be valuable for vaporizer run-time/maintenance analysis (service metrics), liquid leak detection, precise determination of amount of liquid anesthetic remaining and available for delivery, vaporization efficiency calculations, etc. Further still, in some examples, a level switch 313 may be included to prevent overfilling of vaporizing chamber 302 with liquid anesthetic agent 310.

An upper portion of vaporizing chamber 302 (e.g., above a surface of liquid anesthetic 310) holds vaporized anesthetic agent. For example, liquid anesthetic agent 310 may have a relatively low boiling point, such as at or around room temperature, such that liquid anesthetic agent 310 may vaporize without additional heat added. However, vaporization may lower a temperature of liquid anesthetic agent 310 due to the latent heat of vaporization, and changes in the temperature of liquid anesthetic agent 310 may result in variations in the amount of vaporized anesthetic agent produced. By activating heating element 308 to heat grid 306, the latent heat of vaporization may be provided for the phase transition from the liquid form of the anesthetic agent to the vapor and to maintain the temperature of liquid anesthetic agent 310 constant, thereby maintaining a substantially constant vaporization rate. As one non-limiting example, the temperature of liquid anesthetic agent may be maintained at 35° C., as will be described below. Further, inductively heated grid 306 may provide a surface for nucleated boiling of liquid anesthetic agent 310 to produce vapor bubbles 312.

A fresh gas flow including one or more medical grade gases, such as oxygen, air, nitrous oxide, and combinations thereof, may enter anesthetic vaporizer system 300 via a first gas passage 336. The fresh gas flow may be provided via one or more gas pipelines (e.g., via pipeline connections 46 shown in FIG. 1C) and/or one or more gas-holding cylinders (e.g., via cylinder yoke 44 of FIG. 1C). A first proportional valve 343 coupled to the first gas passage 336 may be adjusted by controller 325 to control an amount (or flow rate) of fresh gas flowing through the first gas passage 336. First proportional valve 343 may be a variable valve, such a continuously variable valve, that may be adjusted by controller 325 between a plurality of positions ranging from a fully open and a fully closed position. For example, as a degree of opening of first proportional valve 343 increases, an amount (e.g., flow rate) of fresh gas flowing through first gas passage 336 may increase. A first mass flow sensor 341 may be coupled to first gas passage 336 downstream of first proportional valve 343 to measure a flow rate of the fresh gas flow entering the anesthetic vaporizer system 300. For example, first mass flow sensor 341 may be an ultrasonic flow meter. The entirety of the fresh gas flow provided to anesthetic vaporizer system 300 may bypass vaporizing chamber 302.

Anesthetic agent vapor may exit vaporizing chamber 302 via a second gas passage 340 (e.g., a vapor delivery passage). For example, second gas passage 340 may pass through an opening at or near a top of housing 304 and form a junction 342 with first gas passage 336 to fluidically couple the upper portion of vaporizing chamber 302 with first gas passage 336. Second gas passage 340 is shown including a check valve 348. Check valve 348 may be a one-way valve that allows the vaporized anesthetic agent to flow from vaporizing chamber to junction 342 and prevents the vaporized anesthetic agent and/or fresh gas from flowing from junction 342 to vaporizing chamber 302. For example, check valve 348 may open automatically (e.g., without input or adjustment from a controller or operator) to flow the vaporized anesthetic agent toward junction 342 and close automatically to prevent gas flow toward vaporizing chamber 302.

Second gas passage 340 further includes a shut-off valve 350 and a second proportional valve 352 within a manifold heater 354, downstream of check valve 348. Shut-off valve 350 may be an electronically or mechanically actuated valve that is adjusted responsive to input from controller 325 and/or the operator. For example, shut-off valve 350 may be an on-off valve, wherein shut-off valve 350 is actuated to an open (e.g., fully open) position that allows gas flow through shut-off valve 350 or a closed (e.g., fully closed) position that prevents (e.g., blocks) gas flow through shut-off valve 350 in response to an appropriate command signal from controller 325. Shut-off valve 350 may be closed to quickly stop the supply of the anesthetic agent to a patient, for example. Second proportional valve 352 may be a variable valve, such a continuously variable valve, that may be adjusted by controller 325 between a plurality of positions ranging from a fully open and a fully closed position. For example, as a degree of opening of second proportional valve 352 increases, an amount (e.g., flow rate) of vapor flowing from vaporizing chamber 302 to first gas passage 336 (e.g., via second gas passage 340) may increase. Conversely, as the degree of opening of second proportional valve 352 decreases, the amount of vapor delivered from vaporizing chamber 302 to first gas passage 336 may decrease. Manifold heater 354 may heat shut-off valve 350 and second proportional valve 352 to prevent condensation of the vaporized anesthetic agent in the valves. As a non-limiting example, manifold heater 354 may be operated to maintain shut-off valve 350 and second proportional valve 352 at a substantially constant temperature, such as 40° C.

The fresh gas flow, containing no vaporized anesthetic agent, and the vaporized anesthetic agent from vaporizing chamber 302 mix at and downstream of junction 342. The mixed gas may then be delivered to the patient via an inspiratory limb of a breathing circuit (e.g., via the inspiratory port described with respect to FIG. 1B). A second mass flow sensor 344 may be coupled to first gas passage 336 downstream of the junction 342 with second gas passage 340 to measure a flow rate of the mixed gas exiting the anesthetic vaporizer system 300. For example, second mass flow sensor 344 may be an ultrasonic flow meter or a calorimetric (thermal) mass flow meter. In the case of an ultrasonic flow metering architecture, the output anesthetic agent concentration may be calculated by the difference in the measured TOF between upstream ultrasonic flow sensor 341 and downstream ultrasonic flow sensor 344. Further, an independent concentration sensor 356 may be coupled to first gas passage 336 downstream of the junction 342 with second gas passage 340. Concentration sensor 356 may be any suitable sensor that is configured to measure a concentration of the anesthetic agent in the mixed gas. In one example, concentration sensor 356 may be an optical sensor that transmits light of a suitable wavelength (e.g., infrared) through the mixed gas and determines a concentration of the anesthetic agent based on an absorption of the light by the mixed gas. In other examples, the concentration sensor may be a carbon dioxide or oxygen sensor that measures the concentration of the anesthetic agent based on a displacement of the carbon dioxide or oxygen relative to a supplied concentration of carbon dioxide or oxygen in the fresh gas flow. Concentration sensor 356 may output a signal to controller 325 indicative of the measured concentration of the anesthetic agent (e.g., the concentration of the anesthetic agent vapor) in the mixed gas.

In addition to receiving signals output by level sensor 324, concentration sensor 356, first mass flow sensor 341, and second mass flow sensor 324, controller 325 may receive additional signals, including a measured level of liquid anesthetic agent 310 within sump 322 from a level sensor 321, which may be an infrared level sensor, for example; a measured vapor pressure inside vaporizing chamber 302 ($P_{gas}$) from a pressure sensor 330 coupled to an upper portion of vaporizing chamber 302; a measured fresh gas flow pressure (P1) from a pressure sensor coupled to second gas passage 338 upstream of junction 342; a measured vapor temperature inside vaporizing chamber 302 ($T_{gas}$) from a temperature sensor 332 coupled to an upper portion of vaporizing chamber 302; a measured temperature of grid 306 ($T_{grid}$) from a temperature sensor 328 coupled to grid 306; and a measured temperature of liquid anesthetic agent 310 ($T_{liquid}$) from a temperature sensor 329 that is immersed in the liquid anesthetic agent. Controller 325 receives the signals from the various sensors of FIG. 3, processes the input data, and employs the various actuators of FIG. 3 to adjust operation of anesthetic vaporizer system 300 based on the received signals and instructions stored on a memory of the controller. For example, controller 325 may receive the measured concentration of the anesthetic agent from concentration sensor 356 and adjust a position of one or more of the first proportional valve 343 and the second proportional valve 352, as described further below with respect to FIG. 7. As another example, controller 325 may receive $T_{grid}$ from temperature sensor 328, $T_{liquid}$ from temperature sensor 329 and a current or voltage supplied to heating element 308 based on the input measurements, as further described below with respect to FIG. 8.

Further, data may be input to controller 325 by the operator of anesthetic vaporizer system 300 via a user input device 326 that is operationally connected to the controller and thus configured to transmit an input signal to controller 325 (e.g., via wired or wireless communication). User input device 326 may include one or more of a mouse, a keyboard, a voice input device, a touch input device for receiving a gesture from the operator, a motion input device for detecting non-touch gestures and other motions by the operator, and other comparable input devices, as well as associated processing elements capable of receiving user input from the operator.

Further still, controller 325 may calculate a concentration of the anesthetic agent output by anesthetic vaporizer system 300 and delivered to the patient according to the equation:

$$\% \text{ Agent} = \frac{Fv\left(\frac{VPa}{Pb - VPa}\right)}{Ft \times 1000} \times 100$$

where % Agent is a percentage concentration of the anesthetic agent in the inspiratory limb of the breathing circuit, Fv is a measured flow of gas through the vaporizer (in mL/min, such as measured by second mass flow sensor 344), Ft is a total fresh gas flow into the vaporizer (in L/min, such as measured by first mass flow sensor 341), VPa is a vapor pressure of the volatile anesthetic agent (in mmHg), and Pb is barometric (e.g., ambient) pressure (in mmHg). The vapor pressure of the volatile anesthetic agent may be a known property of the anesthetic agent at a given temperature (e.g., as measured by temperature sensor 329) that is stored in a memory of the controller, for example, in a look-up table. As an example, the operator may input the used anesthetic agent to the controller via the input device. Pb may be measured by an ambient pressure sensor or estimated. The calculated concentration may be used as a sanity check against the concentration of the anesthetic agent measured by concentration sensor 356, for example.

Next, FIGS. 4A-4B show a first cross sectional view 400 and a second cross sectional view 450, respectively, of a vaporizing chamber 402, which may be included in an anesthetic vaporizer system. Vaporizing chamber 402 is a non-limiting example of vaporizing chamber 202 shown in FIG. 2 and/or vaporizing chamber 302 shown in FIG. 3. Reference axes 499 are provided to describe the relative arrangement of components. First view 400 of FIG. 4A is a side view in the x-z plane and is a two-dimensional (2D) representation of three-dimensional (3D) objects. Second view 450 is a perspective view, as indicated by reference axes 499.

A grid 406 is shown disposed within vaporizing chamber 402, such as within an interior of a housing 404 of vaporizing chamber 402. Grid 406 may be grid 206 of FIG. 2 or grid 306 of FIG. 3, for example. Grid 406 may be inductively heated by a heating element 408 (which may be heating element 206 shown in FIG. 2 or heating element 306 shown in FIG. 3, for example), shown as an inductive heating coil. The positioning of grid 406 within housing 404, and therefore relative to heating element 408, may be optimized to provide a desired heating effect for a given heater power. For example, a magnetic field produced by heating element 408 drops proportionally to the square of a radial distance from the heating element. As such, a relatively large radial distance between grid 406 and heating element 408 may result in a relatively low and/or slow temperature increase of grid 406 even at a relatively high heater power of heating element 408. Accordingly, the grid 406 may be sized and/or shaped to position at least an outer circumference of the grid 406 within a threshold distance of the housing 404 and hence the heating element 408, where the threshold distance is relatively small. In one example, the threshold distance between the grid 406 and the housing 404 is in a range from 1-10 mm. In another example, the threshold distance is less than 1 mm. In this way, the grid 406 or other suitable magnetically permeable target (for example, a stainless steel tube) may be positioned in close proximity to the heating element 408 via the wall of housing 404 for efficient energy transfer. For example, as a distance (e.g., radial distance) between the grid 406 and the heating element 408 decreases, energy transfer efficiency increases. Further, as shown in FIGS. 4A and 4B, heating element 408 is positioned exterior to housing 404 at a vertical position (in the z-direction) that overlaps with a vertical position of grid 406 within housing 404. In this way, the heating element 408 substantially surrounds the grid 406 (with housing 404 positioned intermediate the heating element 408 and grid 406).

Grid 406 may be comprised of a wire (or rod) meshwork and a base 410. The base 410 may be specially shaped to interface with the housing 404 of the vaporizing chamber of a vaporizer. Further, the entirety of grid 406 may be comprised of a single, monolithic material, such as metal. Grid 406 may be comprised of a high magnetic permeability material, such as stainless steel. Grid 406 includes a plurality of vertical wires 412 having a length that runs in the z-direction (with respect to reference axes 499), a plurality of horizontal wires 414 having a length that runs in the x-direction (with respect to reference axes 499), and a plurality of circular wires 416 to form the wire meshwork. Vertical wires 412 are perpendicular to horizontal wires 414. Note that in the cross sectional view shown in FIG. 4A, circular wires 416 are represented by cross-sectional circles, and not every circular wire is illustrated.

As particularly shown in second view 450, grid 406 may be cylindrical in shape with a hollow, cylindrical cavity 418 in the center. Circular wires 416 are arranged as evenly spaced concentric circles in a series of coplanar sets (e.g., in the x-y plane with respect to reference axes 499), beginning at cylindrical cavity 418 (e.g., an inner-most circular wire) and ending at a perimeter of grid 406 (e.g., an outer-most circular wire). The coplanar sets are aligned in the x- and y-directions and are vertically distributed (e.g., in the z-direction). For example, the coplanar sets may be equally spaced in the z-direction from a bottom-most coplanar set to a top-most coplanar set.

Horizontal wires 414 extend radially from cylindrical cavity 418 to the perimeter of grid 406 in a series of coplanar sets (e.g., in the x-y plane with respect to reference axes 499). Similar to the coplanar sets of the circular wires 416, the coplanar sets of the horizontal wires 414 are aligned in the x- and y-directions and are vertically distributed (e.g., in the z-direction). Further, each coplanar set of the horizontal wires 414 overlaps with one of the coplanar sets of circular wires 416 such that the horizontal wires 414 and the circular wires 416 intersect. The horizontal wires 414 and the circular wires 416 may be fused at each intersection, for example.

Vertical wires 412 are radially distributed from cylindrical cavity 418 to the perimeter of grid 406 in a series of equally spaced concentric sets. Each concentric set has the same diameter as one of the circular wires 416 such that the vertical wires 412 also intersect with the horizontal wires 414 and the circular wires 416 at each intersection. Vertical wires 412 may also be fused to the horizontal wires 414 and the circular wires 416 at each intersection, for example.

In some embodiments, grid 406 may further include a filter piece having a fine porosity. For example, the filter piece may be positioned at or near the bottom of base 410 and/or within cylindrical cavity 418. When included, base 410 and the filter piece may form a continuous piece, at least in some examples. The filter piece may be configured to receive a carrier gas flow and may generate gas bubbles within liquid anesthetic agent, as described above with respect to FIG. 2. A pore size of the filter piece may be selected to optimize the size of the gas bubbles, such as to maximize the surface area of the carrier gas in contact with the liquid anesthetic agent, and to generate a defined and homogenous gas distribution. The pore size of the filter piece may be further optimized to reduce a pressure drop across the filter piece. Further, the pore size and distribution may be optimized to produce a desired swirl pattern of the produced gas bubbles.

The meshwork of grid 406 provides a high surface area to thermal mass ratio relative to a structure comprised of a solid block of metal or entirely comprised of a highly porous metal filter. The high surface area to thermal mass ratio enables efficient heating by heating element 408 as well as fast thermal response times. For example, the high surface area to thermal mass ratio enables grid 406 to rapidly heat to a desired operating temperature when heating element 408 is powered on and enables grid 406 to quickly cool (e.g., to room temperature) when heating element 408 is turned off. Further, the high surface area to thermal mass ratio enables rapid temperature step changes (e.g., by adjusting the heater power of heating element 408) during anesthetic vaporizer system operation.

Note that in other embodiments, grid 406 may be shaped differently than shown in the embodiment of FIGS. 4A and 4B. For example, the geometry of grid 406 is tunable via additive manufacturing.

Grid 406 may be manufactured using a suitable manufacturing process, such as welding. For example, a first set of concentric circular wires may be welded to a first set of coplanar horizontal wires to form a first circular grid. Then, a set of vertical wires may be welded the first circular grid, such as one vertical wire welded to each intersection of the first circular grid to form a first circular grid structure. A plurality of such circular grid structures may be formed, such as six circular grid structures. Then, each circular grid structure may be welded together to form a stacked grid structure. For example, the first circular grid structure may be welded to a second circular grid structure by welding each unattached end of each vertical wire of the first circular grid structure to a respective intersection of a second circular grid of the second circular grid structure (on a side opposite the vertical wires of the second circular grid structure). Once all the circular grid structures have been welded together, a final circular grid may be welded to the remaining unattached ends of the vertical wires, and the overall grid may be welded to the base and/or a filter in the central cavity. Other manufacturing processes are also possible, such as casting, injection molding, etc.

However, the above-described methods of manufacture of grid 406 may be time-consuming and expensive. Further, some methods of manufacture may be limited in how small the wire diameter and/or spacing of the grid may be, resulting in less desired grid properties that may reduce or slow vaporization of the liquid anesthetic agent. Further still, if different grid geometries are desired, the above-described processes may require new molds or other equipment be manufactured, which may limit the variations that can be made to the grid geometry.

Thus, as described in more detail below, grid 406 may be manufactured using an additive manufacturing process such as 3D printing. By utilizing additive manufacturing, the complex stacked and intersecting grid structure may be manufactured in a fast and low-cost manner, without requiring multiple individual structures that are welded or otherwise fastened together, which may compromise structural integrity. Further, changes to the geometry of the grid, such as changes in wire thickness and/or spacing, as well as changes to the overall dimensions of the grid, may be made by adjusting the model of the grid used as instructions for the additive manufacturing, and without requiring completely different manufacturing equipment. Thus, a variety of different grids may be manufactured for different sized vaporizing chambers and/or for different desired properties, at a large scale and low cost.

Figure 9:
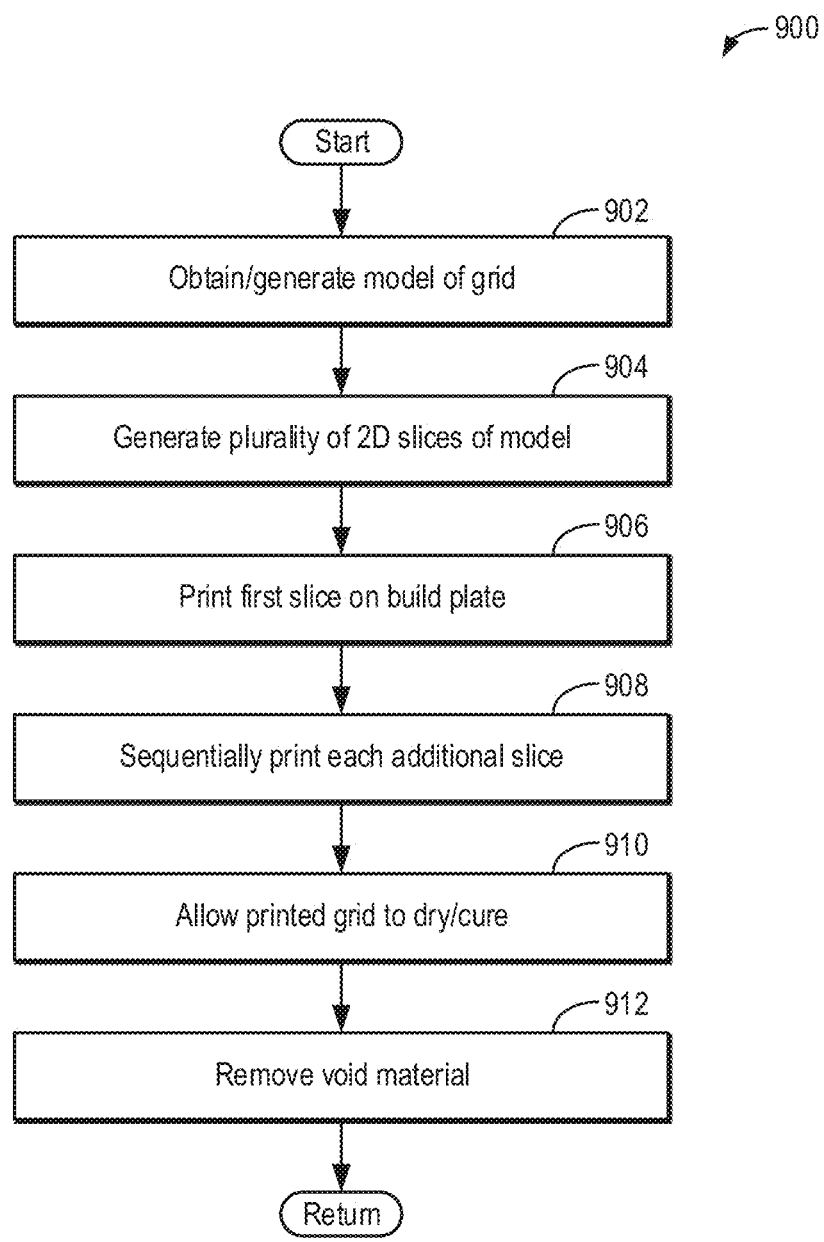
FIG. 9 is a flow chart illustrating an exemplary embodiment of a method for manufacturing a grid configured to be housed in a vaporizing chamber of an anesthetic vaporizer system.

FIG. 9 is a flow chart illustrating an example method 900 for manufacturing a grid configured to be housed in a vaporizing chamber of an anesthetic vaporizer system, such as grid 406 of FIGS. 4A and 4B. Method 900 may be carried out at least in part by a 3D printing device, which may be operatively/communicatively coupled to a printer-interfacing computing device.

At 902, method 900 includes obtaining or generating a 3D model of the grid. The model of the grid may be a computer aided design (CAD) file, additive manufacturing file (AMF), or other 3D modeling file. The 3D model of the grid may be generated on the printer-interfacing computing device. In some examples, the 3D model may be generated entirely from operator instructions via the CAD or other program. In other embodiments, the 3D model may be generated at least in part from information received from a 3D scanner (e.g., a laser scanner) that may image a physical model of the grid. The 3D model may define the dimensions of the grid, exterior and interior structures of the grid, and material properties of the grid, thereby fully representing, in a digital format, the final form of the grid that will be produced. As appreciated by FIGS. 4A and 4B, the grid includes voids (e.g., empty space) and thus the 3D model of the grid may include support structures, fill material, or other features that allow for printing over the voids. The 3D model may include the base portion of the grid and/or the interior filter in order to produce a grid that includes the base portion and/or interior filter integrated with the meshwork of the grid. In other embodiments, the base portion and/or interior filter may be manufactured separately from the meshwork of the grid, and thus may not be included in the 3D model.

At 904, a plurality of 2D slices of the 3D model of the grid are generated. The slices may be generated on the printer-interfacing computing device and then the plurality of slices are sent to the printing device as an STL file, or the 3D model of the grid may be sent to the printing device, and the printing device may slice the 3D model into the plurality of slices to generate an STL file. In doing so, the 3D model is sliced into hundreds or thousands of horizontal layers of a suitable thickness, such as a thickness in a range from 0.1 mm to 3 mm.

At 906, the printing device prints the first slice on a build plate or other suitable base material. When the printing device prints from the STL file, the printing device creates or prints the grid layer-by-layer on the build plate. The printing device reads every slice (or 2D image) from the 3D model and proceeds to create the 3D grid by laying down (or printing) successive layers of material on an upper, planar surface of the build plate until the entire grid is created. Each of these layers can be seen as a thinly sliced horizontal cross section of the eventually completed or printed 3D grid.

The printing device may be a suitable device configured to print metal and/or other high magnetic permeability materials, such as aluminum or stainless steel. The printing device may utilize selective laser melting (SLM) technology, direct metal laser sintering (DMLS) technology, or other suitable metal printing technology. In examples where the voids are initially filled with a dissolvable fill material, the printing device may be configured to print multiple materials (e.g., the metal and the fill material) and thus may include more than one print head.

During printing, the print head(s) is moved, in both horizontal and vertical directions, to complete or print each layer of the 3D model, by a controlled mechanism that is operated by control software running on the printing device, e.g., a computer-aided manufacturing (CAM) software package adapted for use with the printing device. The build plate is typically stationary with its upper planar surface parallel to a horizontal plane, although in some examples the build plate may be moved up and down vertically (i.e., in the z-direction). The printed material solidifies to form a layer (and to seal together layers of the 3D grid), and the print head or build plate is then moved vertically prior to starting the printing of the next layer. This process is repeated until all layers of the 3D grid have been printed.

Accordingly, at 908, each additional slice is sequentially. At 910, the printed grid is dried and/or cured. The drying/curing of the printed grid may be performed after each layer deposition, and/or the drying/curing may be performed after the entire grid is printed. At 912, any void material is removed. For example, if a fill material is printed in the voids, the grid may be placed into water, acid, or other solvent to dissolve the fill material. In another example, if support structures are printed in the voids (e.g., scaffolding-like structures or perforated structures), the support structures may be removed manually and/or with a tool.

Thus, method 900 provides for 3D printing of a grid adapted to be housed in a vaporizing chamber of an anesthetic agent delivery system. While method 900 is directed to printing the entire grid as a single component, in some examples, the 3D model of the grid may include multiple 3D models, each of a different section of the grid. For example, the grid may be divided into a plurality of sections, such as a first section that includes the base portion, a first set of concentric circular wires, a first set of coplanar horizontal wire (that, as described above, may collectively form a first circular grid), and a first set of vertical wires that extend from the first circular grid (which may thereby collectively form a first circular grid structure); a second section that includes a second circular grid section; a third section that includes a third circular grid structure; and so forth. Each section may be printed independently, and then the sections may be stacked and fused together using a suitable mechanism. In such examples, void structures may be reduced or eliminated, which may lower the cost of manufacture.

In still further examples, the grid may be manufactured using a mold. The mold may be generated by first 3D printing a model of the grid in a suitable material that may be solid at room temperature but changes to liquid at a relatively low temperature that is greater than room temperature, such as wax. A plaster mold may be formed over the wax model, and after the plaster dries, the wax may be melted and drained from the mold. The mold may then be filled with molten metal. Once the metal cools, the plaster may be removed to generate the grid.

Thus, the grid described above with respect to FIGS. 4A and 4B may be manufactured using additive manufacturing technology, such as 3D printing. In an example, the grid described herein may be manufactured according to a computer readable medium containing computer readable instructions which, when executed on a 3D printer, cause the printer to print the grid, where the grid comprises a plurality of stacked sets of concentric circular wires, each set of concentric circular wires coupled to a respective set of horizontal wires, each horizontal wire extending outward from a center-most circular wire to an outer-most circular wire. The grid further comprises a set of vertical wires coupled to the sets of concentric circular wires, each vertical wire extending from a top-most set of concentric circular wires to a bottom-most set of concentric circular wires. In some examples, the grid includes a porous filter contained inside the center-most circular wire of each set of concentric circular wires. In some examples, the grid further includes a base portion coupled to the bottom-most set of concentric circular wires and/or the porous filter. In some examples, the grid includes a base shaped to interface with a component of a vaporizing chamber. The grid may be a vaporizer grid for assisting in the vaporization of liquid.

In an example, a method of creating a computer readable 3D model suitable for use in additive manufacturing of a grid configured to be housed in a vaporizing chamber of an anesthetic agent delivery system is provided, wherein the grid comprises a plurality of stacked sets of concentric circular wires, each set of concentric circular wires coupled to a respective set of horizontal wires, each horizontal wire extending outward from a center-most circular wire to an outer-most circular wire. The grid further comprises a set of vertical wires coupled to the sets of concentric circular wires, each vertical wire extending from a top-most set of concentric circular wires to a bottom-most set of concentric circular wires. In an example, the method includes obtaining specifications of the grid. The specifications may be obtained from user input (e.g., via a 3D modeling program such as CAD) and/or from information obtained from a 3D scanner. For example, the 3D scanner may image a physical model or prototype of the grid. The method further includes generating the computer readable 3D model of the grid based on the obtained specifications. The 3D model may be generated using CAD or another 3D modeling program. In some examples, the method further includes sending the 3D model to a printing device. The 3D model may be converted into an STL file or other suitable format readable by the printing device. The printing device may then print the grid according to the specifications set forth by the 3D model. The grid may be grid 406 of FIGS. 4A and 4B, for example.

Figure 5:
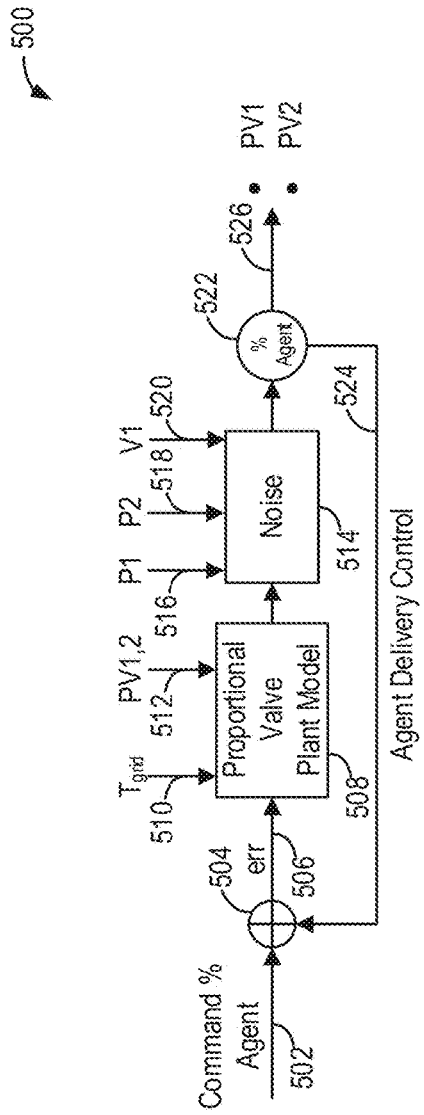
FIG. 5 shows an agent delivery control loop that may be implemented by a controller of an anesthetic vaporizer system.
Figure 6:
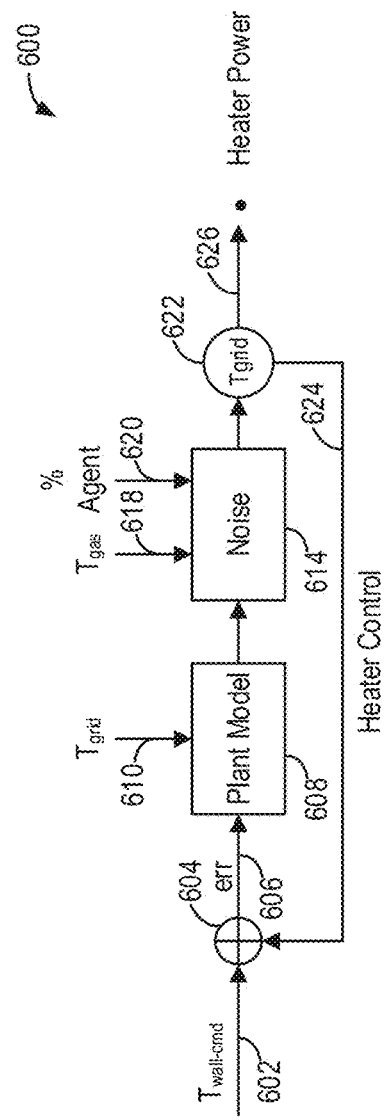
FIG. 6 shows a heater control loop that may be implemented by a controller of an anesthetic vaporizer system.

An anesthetic vaporizer system having a grid heated by an inductive heating element, such as the systems shown in FIGS. 2-4B, may be controlled in various ways to deliver a desired concentration of vaporized anesthetic agent to a patient. In one example, as shown in FIGS. 5 and 6, a controller (e.g., controller 225 of FIG. 2 or controller 325 of FIG. 3) may control agent delivery separately from heater control. For example, the controller may be a proportional-integral-derivative (PID) controller with separate control loops for agent delivery and heater control. As such, in some embodiments, the heater may not be adjusted to vary the amount of vaporized anesthetic produced.

Turning first to FIG. 5, a block diagram of an example agent delivery control loop 500 that may be implemented by the controller is shown. Additionally, the control of the agent delivery will be further described below with respect to FIG. 7. Control loop 500 outputs a commanded position for a first proportional valve in the anesthetic vaporizer system that controls the flow of fresh gas (e.g., first proportional valve 243 of FIG. 2 or first proportional valve 343 of FIG. 3), herein referred to as PV1. Control loop 500 also outputs commanded position for a second proportional valve (e.g., second proportional valve 252 of FIG. 2 or second proportional valve 352 of FIG. 3) that controls the flow of vaporized anesthetic agent from the vaporizer to the junction where the vaporized anesthetic agent mixes with the fresh gas, before being delivered to the patient, herein referred to as PV2. Each of the commanded valve positions (PV1 and PV2) is determined based on a difference between a commanded anesthetic agent concentration and a measured anesthetic agent concentration. Further, the commanded valve positions may take into account a temperature of a grid that vaporizes the anesthetic agent, which may influence the final anesthetic agent concentration, as well as the pressures both upstream and downstream of the junction where the vaporized anesthetic agent mixes with the fresh gas flow and the fresh gas velocity upstream of the junction.

The controller receives a commanded concentration of vaporized anesthetic agent to deliver (e.g., an agent concentration setpoint received via user input, for example) as a command % agent 502. The command % agent 502 is input into a junction 504 along with a % agent feedback signal 524. The % agent feedback signal 524 is from a measured % agent 522 (e.g., as measured by concentration sensor 256 shown in FIG. 2 or concentration sensor 356 shown in FIG. 3). A difference between the command % agent 502 and % agent feedback signal is determined in order to generate a resulting error value 506, which is input into a proportional valve plant model 508.

A temperature of the inductively heated grid ($T_{grid}$) 510 (e.g., as measured by temperature sensor 228 of FIG. 2 or temperature sensor 328 of FIG. 3) and current proportional valve settings 512 are also input into the proportional valve plant model 508. The current proportional valve settings 512 correspond to a position (or setting) of the first proportional valve P1 and the second proportional valve P2.

The proportional valve plant model 508 uses the error 506, the $T_{grid}$ 510, and the current proportional valve settings 512 to update the proportional valve settings. For example, the controller may continuously calculate the error value 506 as the difference between the command % agent 502 and the % agent feedback signal 524 and apply a correction to the proportional valve settings based on proportional, integral, and derivative terms. However, the updated (e.g., corrected) proportional valve settings may be first passed through a noise compensation block 514 along with noise variables. The noise variables include a first pressure (P1) 516 (e.g., as measured by pressure sensor 231 of FIG. 2 or pressure sensor 331 of FIG. 3), a second pressure (P2) 518 (e.g., downstream of the junction where the vaporized anesthetic agent mixes with the fresh gas flow), and a velocity (V1) 520 (e.g., as measured by mass flow sensor 241 of FIG. 2 or mass flow sensor 341 of FIG. 3). The noise compensation block 514 may account for disturbances in the system that may influence the agent concentration (in addition to the proportional valve positions), including the pressures (P1 and P2) of the fresh gas and fresh gas/vaporized anesthetic agent mix and the velocity of the fresh gas flow, for example. The control loop may then output the updated proportional valve settings 526 (e.g., PV1 and PV2). The agent concentration 522 that is measured by the agent concentration sensor is directly affected by the position of the proportional valves, and thus the measured agent concentration is used as the feedback process variable.

Continuing to FIG. 6, a block diagram of an example heater control loop 600 that may be implemented by the controller is shown. Additional heater control will be described below with respect to FIG. 8. Control loop 600 outputs a commanded heater power for the inductive heating element in order to heat the grid to a desired temperature for vaporizing the anesthetic agent. The commanded heater power is determined based on a difference between the desired temperature of the grid and a measured temperature of the grid. Further, the commanded heater power may take into account a temperature of the vaporized anesthetic agent and the commanded concentration of vaporized anesthetic agent to deliver via the anesthetic vaporizer system, which may influence the heater power output. The heater power may also be monitored to act as a corollary to the amount of energy transferred into the grid (e.g., the heated target) via a lookup table, which may be used to prevent overheating of the target. The heater coil inductance may likewise be measured to monitor the health and status of the heater-target system.

The controller receives a commanded temperature of the inductively heated grid ($T_{wall-cmd}$) 602 (e.g., a temperature setpoint, received via user input and/or selected based on user input, for example). The $T_{wall-cmd}$ 602 is input into a junction 604 along with a $T_{grid}$ feedback signal 624. The $T_{grid}$ feedback signal 624 is from a measured $T_{grid}$ 622 (e.g., as measured by temperature sensor 228 of FIG. 2 or temperature sensor 328 of FIG. 3). A difference between the $T_{wall-cmd}$ 602 and the $T_{grid}$ feedback signal 624 is determined in order to generate a resulting error value 606, which is input into a plant model 608, which also receives the currently measured $T_{grid}$ as an input 610. For example, $T_{grid}$ input 610 may be included in addition to the measured $T_{grid}$ 622 for redundancy and error trapping (e.g., $T_{grid}$ input 610 and measured $T_{grid}$ 622 temperatures that are not within a threshold range of each other, such as within 2° C., may indicate a temperature sensor error). The plant model 608 uses the error 606 and the $T_{grid}$ input 610 to update a heater power command to the inductive heating element. For example, the controller may continuously calculate the error value 606 as the difference between the $T_{wall-cmd}$ 602 and the $T_{grid}$ feedback signal 624 and apply a correction to the commanded heater power output based on proportional, integral, and derivative terms.

Figure 7:
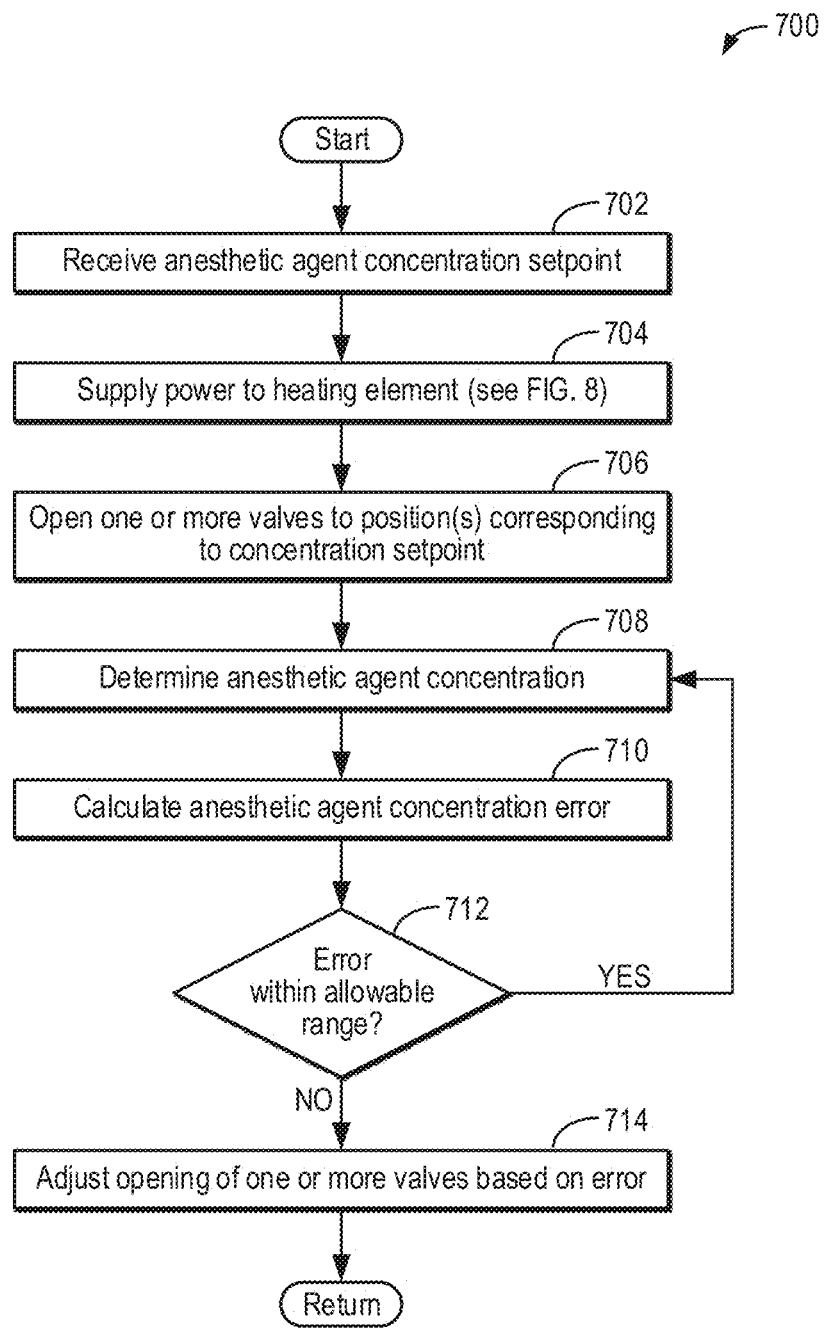
FIG. 7 is a flow chart illustrating an exemplary embodiment of a method for controlling an amount of vaporized anesthetic agent delivered to a patient via an anesthetic vaporizer system including a heating element.

However, the updated heater power command may be first passed through a noise compensation block 614 along with noise variables. The noise variables include a measured vapor temperature inside vaporizing chamber ($T_{gas}$) 618 (e.g., as measured by temperature sensor 232 shown in FIG. 2 or temperature sensor 332 shown in FIG. 3) and the measured % agent 620. The noise compensation block 614 may account disturbances in the system that may influence $T_{grid}$ (other than the heater output of the heating element), including variations in the $T_{gas}$ and the measured % agent (e.g., as measured by concentration sensor 256 shown in FIG. 2 or concentration sensor 356 shown in FIG. 3), for example. The control loop may then output the updated heater power command 626. The measured $T_{grid}$ 622 that is measured by the temperature sensor coupled to the heated grid is directly affected by the heater power output by the heating element, and thus the measured temperature of the grid is used as the feedback process variable Next, FIG. 7 shows a method 700 for operating an anesthetic vaporizer system that includes an inductively heated grid submerged within liquid anesthetic agent in a vaporizing chamber, such as the anesthetic vaporizer systems of FIGS. 2-4B, to deliver a desired concentration of vaporized anesthetic agent to a patient. Method 700 may be carried out by a controller, such as controller 225 of FIG. 2 or controller 325 of FIG. 3, according to instructions stored in a memory of the controller and in conjunction with one or more sensors (e.g., concentration sensor 256 of FIG. 2 or concentration sensor 356 of FIG. 3) and actuators (e.g., heating element 208 of FIG. 2 or heating element 308 of FIG. 3, first proportional valve 243 of FIG. 2 or first proportional valve 343 of FIG. 3, second proportional valve 252 of FIG. 2 or second proportional valve 352 of FIG. 3). For example, electrical power may be supplied to the heating element to heat the metal grid to a desired temperature for facilitating vaporization of the liquid anesthetic agent, and one or more valves may be adjusted to control the concentration of the vaporized anesthetic agent that is delivered to the patient. As an example, method 700 may be performed in response to a request to deliver anesthetic agent to the patient (e.g., based on user input).

At 702, an anesthetic agent concentration setpoint is received. The anesthetic agent may be any suitable volatile liquid anesthetic agent, such as desflurane, isoflurane, sevoflurane, or the like, or another medication that may be nebulized/inhaled, such as albuterol. The concentration setpoint may be a percentage of the vaporized anesthetic agent per volume of a fresh gas/vaporized anesthetic agent mix provided to the patient. The concentration setpoint, referring to the desired concentration of anesthetic agent to deliver to the patient, may be obtained via user input to the controller (e.g., via input device 226 of FIG. 2 or input device 326 of FIG. 3) or via another suitable mechanism.

At 704, method 700 includes supplying power to the heating element. As described with respect to FIG. 2, the heating element may be an inductive heating element that is configured to selectively increase a temperature of the grid to a desired temperature. In some examples, the desired temperature may be a pre-determined setpoint temperature for the type anesthetic agent used. As described above with respect to FIGS. 5 and 6, an amount of power supplied to the heating element may be controlled independently of controlling the amount of anesthetic agent delivered to the patient. An example heater control routine is described below with respect to FIG. 8. By supplying power to the heating element, liquid anesthetic agent within the vaporizing chamber of the anesthetic vaporizer system may be efficiently vaporized.

At 706, method 700 includes opening one or more valves based on the anesthetic agent concentration setpoint. For example, the anesthetic vaporizer system may include one or more proportional valves and one or more shut-off valves for controlling gas flow through the anesthetic vaporizer. For example, the first proportional valve, which controls an amount (or flow rate) of fresh gas entering the anesthetic vaporizer system, may be adjusted to a default open position. As another example, the controller may adjust the open position of the first proportional valve based on the anesthetic agent concentration setpoint. For example, the controller may input the anesthetic agent concentration setpoint into one or more look-up tables, functions, or algorithms, which may then output the position (or setting) of the first proportional valve. The controller may then transmit a command signal to the first proportional valve to adjust the first proportional valve to the output position. As an example, as the anesthetic agent concentration setpoint increases, a degree of opening of the first proportional valve may increase to enable a higher flow rate of fresh gas through the anesthetic vaporizer system.

Similarly, an open position of the second proportional valve, which controls an amount (or flow rate) of vaporized anesthetic agent flowing from the vaporizing chamber, may be determined based on the anesthetic agent concentration setpoint. For example, the controller may input the anesthetic agent concentration setpoint into one or more look-up tables, functions, or algorithms, which may then output the position (or setting) of the second proportional valve. In some embodiments, the controller may further account for the setting of the first proportional valve and/or a measured fresh gas flow into the vaporizer system (e.g., as measured by first mass flow sensor 241 of FIG. 2 or first mass flow sensor 341 of FIG. 3), such as by inputting the setting of the first proportional valve position and/or the measured fresh gas flow into the one or more look-up tables, functions, or algorithms. The controller may then transmit a command signal to the second proportional valve to adjust the second proportional valve to the output position. As an example, as the anesthetic agent concentration setpoint increases, a degree of opening of the second proportional valve may increase to flow a larger amount of vaporized anesthetic agent from the vaporizing chamber. Further, shut-off valves, such as shut-off valves 246 and 250 of FIG. 2 or shut-off valve 350 of FIG. 3, may be actuated to their fully open positions.

At 708, method 700 includes determining the anesthetic agent concentration. For example, the concentration of the anesthetic agent supplied to the patient may be measured by the concentration sensor, which may be positioned in a gas outlet passage of the anesthetic vaporizer system (e.g., first gas passage 236 of FIG. 2 or first gas passage 336 of FIG. 3). The concentration sensor may output a signal corresponding to the measured concentration of the anesthetic agent to the controller.

At 710, method 700 includes determining an anesthetic agent concentration error. The anesthetic agent concentration error may be the difference between the setpoint agent concentration and the measured agent concentration. For example, the anesthetic agent concentration error (ERR) may be calculated as:

$$ERR = Agent_{actual} - Agent_{setpoint}$$

where $Agent_{actual}$ is the concentration of the anesthetic agent supplied to the patient (e.g., as determined at 708) and $Agent_{setpoint}$ is the anesthetic agent concentration setpoint (e.g., as received at 702).

At 712, method 700 includes determining if the anesthetic agent concentration error is within an allowable range. As an example, the allowable range may be defined by a lower threshold value and an upper threshold value. In some examples, the lower threshold value may be an anesthetic agent concentration error value that corresponds to an anesthetic agent concentration value that is a percentage below the anesthetic agent concentration setpoint, and the upper threshold value may be an anesthetic agent concentration error value that corresponds to an anesthetic agent concentration value that is the percentage above the anesthetic agent concentration setpoint. Thus, the allowable range may encompass anesthetic agent concentration error values that correspond to the concentration of the anesthetic agent supplied to the patient remaining within the percentage of the anesthetic agent concentration setpoint. In some examples, the percentage may vary based on one or more of the anesthetic agent concentration setpoint and the anesthetic used, such that the percentage may be smaller when the anesthetic used is more precisely controlled.

If the anesthetic agent concentration error is within the allowable range, method 700 returns to 708 and includes continuing to determine the anesthetic agent concentration. In this way, the anesthetic agent concentration error may be updated as the anesthetic agent concentration supplied to the patient changes. If the anesthetic agent concentration error is not within the allowable range, method 700 proceeds to 714 and includes adjusting the opening of the one or more valves based on the error. For example, if the error indicates the measured anesthetic agent concentration is less than the concentration setpoint (and outside of the allowable range), the opening of the first proportional valve and/or the second proportional valve may be increased to increase the amount of vaporized anesthetic agent flowing from the vaporizing chamber and delivered to the patient. Conversely, if the error indicates the measured anesthetic agent concentration is greater than the concentration setpoint (and outside of the allowable range), the opening of the first proportional valve and/or the second proportional valve may be decreased to decrease the amount of vaporized anesthetic agent flowing from the vaporizing chamber and delivered to the patient. In one example, the proportional valve settings may be adjusted using a proportional-integral-derivative controller to drive the measured agent concentration toward the concentration setpoint, as described above with respect to FIG. 5. Additionally, in some embodiments, the opening of the one or more valves may be further adjusted based on noise variables in the system, such as fresh gas flow rate and pressure and/or temperature of the inductive heating grid. In some embodiments, the anesthetic vaporizer system may include a pressure regulator (e.g., pressure regulator 242 of FIG. 2) that controls a gas pressure in the vaporizing chamber, thus fixing a gas pressure boundary condition for the second proportional valve. In such an example, the second proportional valve may be adjusted based on the anesthetic agent concentration error while the first proportional valve is not adjusted. In other embodiments, such as where the anesthetic vaporizer system does not include the pressure regulator (such as anesthetic vaporizer system 300 shown in FIG. 3), the first proportional valve and the second proportional valve may be adjusted simultaneously via a feedback control loop, thereby achieving a same net effect of using the pressure regulator and the second proportional valve. Method 700 then returns to continue measuring the anesthetic agent concentration and adjusting the opening of the one or more valves based on the error between the setpoint and measured agent concentration until the system is deactivated and anesthetic agent is no longer supplied to the patient.

Figure 8:
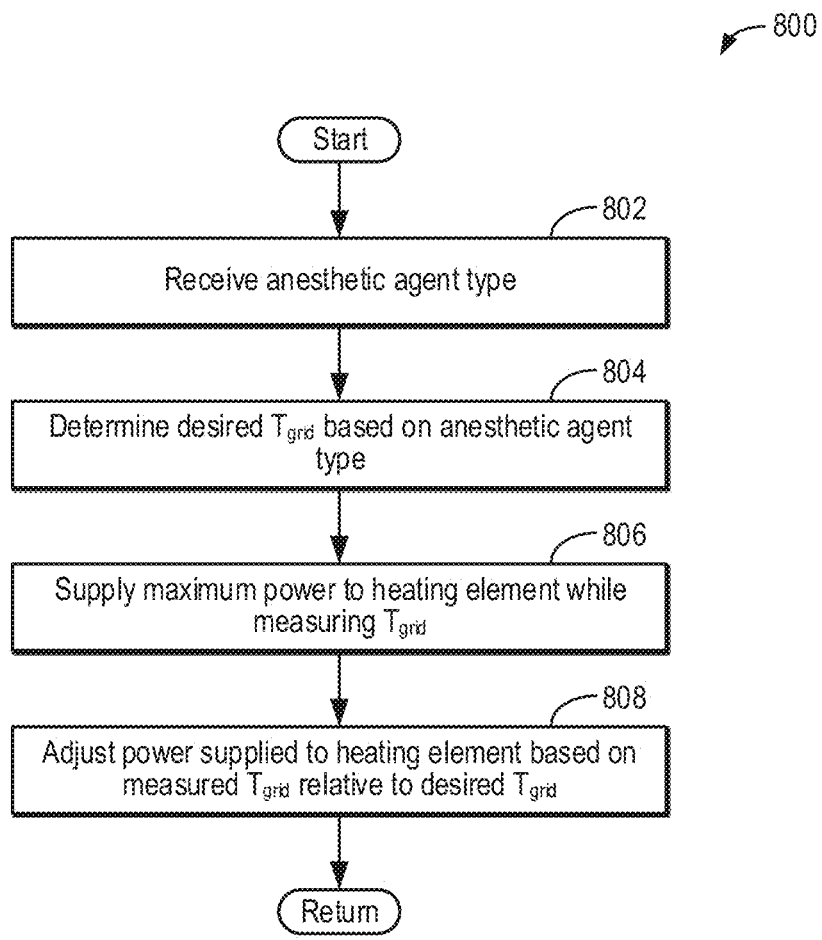
FIG. 8 is a flow chart illustrating an exemplary embodiment of a method for controlling an output power of a heating element of an anesthetic vaporizer system.

Turning now to FIG. 8, a method 800 for operating a heating element of an anesthetic vaporizer system, such as the anesthetic vaporizer systems of FIGS. 2-4B, is shown. As one example, method 800 may be performed as a part of method 700 of FIG. 7 (e.g., at 704) in order to facilitate vaporization of a liquid anesthetic agent by heating a grid disposed within a vaporizing chamber of the anesthetic vaporizer system and submerged within the liquid anesthetic agent. Method 800 may be carried out by a controller, such as controller 225 of FIG. 2 or controller 325 of FIG. 3, according to instructions stored in a memory of the controller and in conjunction with one or more sensors (e.g., temperature sensor 228 of FIG. 2 or temperature sensor 328 of FIG. 3) and actuators (e.g., heating element 208 of FIG. 2 or heating element 308 of FIG. 3).

At 802, method 800 includes receiving an indication of the type of anesthetic agent used. The type of anesthetic agent may refer to the particular anesthetic agent currently contained within the anesthetic vaporizer system (e.g., desflurane, isoflurane, or sevoflurane). In some examples, the controller may further receive an anesthetic agent concentration setpoint. The concentration setpoint may be a percentage of the vaporized anesthetic agent per volume of a fresh gas/vaporized anesthetic agent mix to provide to a patient (e.g., a desired concentration of anesthetic agent to deliver to the patient). The type of anesthetic agent and, in some examples, the anesthetic agent concentration setpoint, may be obtained via user input to the controller (e.g., via input device 226 of FIG. 2 or input device 326 of FIG. 3) or via another suitable mechanism.

At 804, method 800 includes determining a desired temperature of the grid ($T_{grid}$) based on the anesthetic agent type. Similarly, the controller may additionally determine a desired temperature of the liquid anesthetic agent ($T_{liquid}$) based on the anesthetic agent type. For example, each anesthetic agent type may have a first corresponding pre-determined temperature setpoint as the desired $T_{grid}$ and a second pre-determined temperature setpoint as the desired $T_{liquid}$. As an example, as a boiling point of the anesthetic agent increases, the desired $T_{grid}$ and the desired $T_{liquid}$ may increase. The controller may input the anesthetic agent type into a look-up table stored in memory, which may output the desired $T_{grid}$ and/or the desired $T_{liquid}$, for example. As another example, the controller may further adjust the desired $T_{grid}$ and/or the desired $T_{liquid}$ based on the anesthetic agent concentration setpoint. For example, as the anesthetic agent concentration setpoint increases, the desired $T_{grid}$ may be increased above the pre-determined $T_{grid}$ setpoint. Similarly, as the anesthetic agent concentration setpoint increases, the desired $T_{liquid}$ may be increased above the pre-determined $T_{liquid}$ setpoint. The controller may input the anesthetic agent concentration setpoint into one or more look-up tables, functions, or algorithms, which may output the desired $T_{grid}$ and/or the desired $T_{liquid}$, or the temperature adjustment to the $T_{grid}$ setpoint and/or the $T_{liquid}$ setpoint, for the given anesthetic agent type, for example.

At 806, method 800 includes supplying maximum power to the heating element while measuring $T_{grid}$. Similarly, $T_{liquid}$ can be monitored to provide similar or additional information for a flexible and well-monitored heat transfer system. For example, in order to heat the grid from an ambient temperature to the desired $T_{grid}$ as quickly as possible, and thereby reduce an amount of time before the vaporized anesthetic agent can be delivered to the patient, a power source may output a maximum voltage and a maximum current to the heating element. As another example, resonant inductive coupling may be used, and the heating element may be operated at its resonance frequency to increase power transfer to the heating element, and thereby produce maximum heating of the grid. The maximum power may continue to be supplied to the heating element until $T_{grid}$ reaches or approaches (e.g., comes within a percentage of) the desired $T_{grid}$, for example.

At 808, method 800 includes adjusting the power supplied to the heating element based on the measured $T_{grid}$ relative to the desired $T_{grid}$. For example, the heating element may include a variable frequency drive to vary the heating element voltage (or current) and frequency, such as via pulse-width modulation (PWM). As another example, the operation of the heating element may be phase-shifted from the resonance frequency to decrease the heater output power. The controller may determine a drive voltage and frequency (e.g., duty cycle of voltage) to supply to the heating element based on the desired $T_{grid}$, such as by inputting the desired $T_{grid}$ into a look-up table, algorithm, or function, which may output the drive voltage and frequency, for example. The controller may then provide voltage to the heating element at the determined drive voltage and frequency. Then, the controller may further adjust the drive voltage and frequency based on the measured $T_{grid}$ relative to the desired $T_{grid}$, for example, using a proportional-integral-derivative controller to drive the measured $T_{grid}$ to the desired $T_{grid}$, as described above with respect to FIG. 6.

Similarly, $T_{liquid}$ may be used for heater power control in addition to or as an alternative to $T_{grid}$. $T_{liquid}$ has multiple impacts a control variable. For example, maintaining $T_{liquid}$ at or above a maximum room temperature specification of the anesthetic agent type used may increase a consistency of the amount of anesthetic agent output by the anesthetic vaporizer system. As another example, for anesthetic agents with a relatively high vapor pressure (e.g., desflurane), controlling $T_{liquid}$ controls the gas pressure in the vaporizing chamber. As still another example, when medical gas is bubbled through the liquid anesthetic agent (e.g., as described with respect to FIG. 2), a difference between a temperature of the gas, which may be approximately equal to $T_{grid}$ when a gas bubble is formed, and $T_{liquid}$ directly controls a rate and effectiveness of agent vapor mass transport into the gas bubble. Therefore, the controller may further adjust the drive voltage and frequency based on the measured $T_{liquid}$ relative to the desired $T_{liquid}$ in order to drive the measured $T_{liquid}$ to the desired $T_{liquid}$. Method 800 then returns to continue measuring $T_{grid}$ (and/or $T_{liquid}$) and adjusting the power supplied to the heating element based on the error between the desired $T_{grid}$ (and/or $T_{liquid}$) and the measured $T_{grid}$ (and/or $T_{liquid}$) until the system is deactivated and anesthetic agent is no longer supplied to the patient.

Thus, the systems and methods described herein provide for an inductively heated anesthetic vaporizer system. In some examples, the anesthetic vaporizer system may be a bubble-through anesthetic vaporizer, wherein carrier gas bubbles and liquid anesthetic agent are heated by an inductively heated grid. In other examples, such as when a low boiling point anesthetic agent is used, carrier gas may not be bubbled through the anesthetic vaporizer system. By heating the grid inductively, a quicker response time may be provided than bulk boiling the anesthetic agent and/or using conductive heating, and a smaller amount of energy may be consumed. Further, a temperature of the grid may be step-controlled due to the inductive heating. Further still, by bubbling gas through the inductively heated grid, the gas may become uniformly saturated with the vaporized anesthetic agent. Further still, high concentrations of anesthetic agent at high flow rates may be maintained with high accuracy and simplified control loops.

A technical effect of submerging an inductively heated grid within liquid anesthetic agent is that the temperature of the grid may be rapidly changed while power consumption is reduced to efficiently vaporize the anesthetic agent.

In one embodiment, a system for an anesthesia vaporizer comprises: a vaporizing chamber configured to hold a liquid anesthetic agent; a grid disposed within the vaporizing chamber; and a heating element positioned relative to the vaporizing chamber and configured to increase the temperature of the grid. In a first example of the system, the heating element is an inductive heating element positioned exterior to the vaporizing chamber and the grid is comprised of metal. In a second example of the system, which optionally includes the first example, the grid is fully submerged in the liquid anesthetic agent while the anesthesia vaporizer is operated to deliver anesthetic agent to a patient. A third example of the system, which optionally includes one or both of the first and second examples, further comprises a controller storing executable instructions in non-transitory memory that, when executed, cause the controller to: adjust an amount of power provided to the heating element based on a desired temperature of the grid relative to a measured temperature of the grid and/or a desired temperature of the liquid anesthetic agent relative to a measured temperature of the liquid anesthetic agent. In a fourth example of the system, which optionally includes one or more or each of the first through third examples, the measured temperature of the grid is measured by a temperature sensor coupled to the grid and the measured temperature of the liquid anesthetic agent is measured by a temperature sensor immersed in the liquid anesthetic agent, and the desired temperature of the grid is selected from a plurality of preset temperatures stored in memory based on user input. In a fifth example of the system, which optionally includes one or more or each of the first through fourth examples, the instructions that cause the controller to adjust the amount of power provided to the heating element based on the desired temperature of the grid relative to the measured temperature of the grid include further instructions stored in non-transitory memory that, when executed, cause the controller to: determine a drive voltage and frequency of the heating element based on the desired temperature of the grid; operate the heating element at the determined drive voltage and frequency; increase the drive voltage and frequency from the determined drive voltage and frequency in response to the measured temperature of the grid being less than the desired temperature of the grid; and decrease the drive voltage and frequency from the determined drive voltage and frequency in response to the measured temperature of the grid being greater than the desired temperature of the grid. A sixth example of the system, which optionally includes one or more or each of the first through fifth examples, further comprises a first gas passage configured to flow medical gas through the anesthesia vaporizer; and a first proportional valve disposed within the first gas passage and configured to control a flow rate of the medical gas through the anesthesia vaporizer. A seventh example of the system, which optionally includes one or more or each of the first through sixth examples, further comprises a second gas passage that fluidically couples the first gas passage from downstream of the first proportional valve to the grid, the second gas passage configured to flow a portion of the medical gas from the first gas passage to the grid, a pressure in the second gas passage controlled by an upstream pressure regulator. An eighth example of the system, which optionally includes one or more or each of the first through seventh examples, further comprises a vapor delivery passage coupled between a top portion of the vaporizing chamber and first gas passage, forming a junction with the first gas passage downstream of the first proportional valve, to fluidically couple the top portion of the vaporizing chamber with the first gas passage; a second proportional valve disposed within the vapor delivery passage and configured to control a flow rate of vapor from the vaporizing chamber to the first gas passage. In a ninth example of the system, which optionally includes one or more or each of the first through eighth examples, the controller stores further executable instructions in non-transitory memory that, when executed, cause the controller to: adjust a position of one or more of the first proportional valve and the second proportional valve based on a measured anesthetic agent concentration relative to a desired anesthetic agent concentration. In a tenth example of the system, which optionally includes one or more or each of the first through ninth examples, the measured anesthetic agent concentration is measured by a concentration sensor coupled to the first gas passage downstream of the junction and the desired anesthetic agent concentration is received from user input, and the instructions that cause the controller to adjust the position of one or more of the first proportional valve and the second proportional valve based on the measured anesthetic agent concentration relative to the desired anesthetic agent concentration include further instructions stored in non-transitory memory that, when executed, cause the controller to: determine a first open position as a valve setting of the first proportional valve and a second open position as a valve setting of the second proportional valve based on the desired anesthetic agent concentration; operate the anesthesia system with the first proportional valve commanded to the valve setting of the first proportional valve and the second proportional valve commanded to the valve setting of the second proportional valve; adjust the valve setting of the first proportional valve to a third open position, less open than the first open position, and/or adjust the valve setting of the second proportional valve to a fourth open position, less open than the second open position, in response to the measured anesthetic agent concentration being greater than the desired anesthetic agent concentration; and adjust the valve setting of the first proportional valve to a fifth open position, more open than the first open position, and/or adjust the valve setting of the second proportional valve to a sixth open position, more open than the second open position, in response to the measured anesthetic agent concentration being less than the desired anesthetic agent concentration.

In another embodiment, a method for an anesthetic vaporizer comprises: supplying power to an inductive heating element configured to heat a grid disposed within a vaporizing chamber of the anesthetic vaporizer, the grid submerged within an anesthetic agent; and adjusting one or more valves to adjust a concentration of the anesthetic agent output by the anesthetic vaporizer. In a first example of the method, supplying power to the inductive heating element comprises: initially supplying maximum power to the inductive heating element to heat the grid from an ambient temperature to a desired temperature; supplying a less than maximum power to the inductive heating element responsive to a measured temperature of the grid reaching the desired temperature, the less than maximum power determined based on the desired temperature; and further adjusting the power supplied to the inductive heating element based on a difference between the measured temperature of the grid and the desired temperature. In a second example of the method, which optionally includes the first example, adjusting the power supplied to the inductive heating element based on the difference between the measured temperature of the grid and the desired temperature comprises: reducing the power supplied to the inductive heating element from the less than maximum power responsive to the measured temperature being greater than the desired temperature; and increasing the power supplied to the inductive heating element from the less than maximum power responsive to the measured temperature being less than the desired temperature. In a third example of the method, which optionally includes one or both of the first and second examples, adjusting the one or more valves to adjust the concentration of the anesthetic agent output by the anesthetic vaporizer comprises: actuating a first proportional valve, configured to adjust a gas flow into the anesthetic vaporizer, to a first position determined based on a concentration setpoint; actuating a second proportional valve, configured to adjust a flow of the anesthetic agent vaporized in the vaporizing chamber output to the gas flow, to a second position determined based on the concentration setpoint; and adjusting at least one of the first proportional valve and the second proportional valve based on a difference between the concentration of the anesthetic agent output by the anesthetic vaporizer and the concentration setpoint.

In another embodiment, a system for an anesthesia machine comprises: an anesthetic vaporizer, the anesthetic vaporizer including a vaporizing chamber having a meshwork grid disposed therein; an inductive heating coil arranged exterior to the vaporizing chamber at a vertical position that overlaps with a vertical position of the meshwork grid; a vapor delivery passage that fluidically couples the vaporizing chamber to a patient breathing circuit; a valve disposed in the vapor delivery passage; and a controller storing executable instructions in non-transitory memory that, when executed, cause the controller to: supply power to the inductive heating coil to heat the meshwork grid to a temperature setpoint selected based on a type of anesthetic agent within the vaporizing chamber; actuate the valve to a valve setting selected based on a desired concentration of anesthetic agent to output to the patient breathing circuit; and adjust each of the power supplied to the inductive heating coil and the valve setting based on a corresponding electronic feedback signal. A first example of the system further comprises a level sensor coupled to the vaporizing chamber, the level sensor configured to measure a level of the anesthetic agent in the vaporizing chamber, and a pump configured to supply the anesthetic agent to the vaporizing chamber from a sump, and the controller stores further executable instructions in non-transitory memory that, when executed, cause the controller to: operate the pump to maintain the level of the anesthetic agent in the vaporizing chamber within a desired range based on output from the level sensor. In a second example of the system, which optionally includes the first example, the meshwork grid comprises: a central cylindrical cavity; a plurality of vertical wires, the plurality of vertical wires radially distributed from the central cylindrical cavity to a perimeter the meshwork grid in a series of equally spaced concentric sets; a plurality of horizontal wires, the horizontal wires perpendicular to the vertical wires and extending radially from the central cylindrical cavity to the perimeter of the meshwork grid in a series of coplanar sets; and a plurality of circular wires, the plurality of circular wires arranged in a plurality of concentric, coplanar sets that are aligned horizontally and equally distributed vertically. In a third example of the system, which optionally includes one or both of the first and second examples, each of the plurality of circular wires intersects with all of the horizontal wires of a single coplanar set and all of the vertical wires of a single concentric set. In a fourth example of the system, which optionally includes one or more or each of the first through third examples, the meshwork grid further comprises a porous filter coupled to the central cylindrical cavity at a base of the meshwork grid.

In another representation, a system for an anesthesia machine comprises: an anesthetic vaporizer, the anesthetic vaporizer including a vaporizing chamber; an inductive heating coil arranged exterior to the vaporizing chamber; a vapor delivery passage that fluidically couples the vaporizing chamber to a patient breathing circuit; a valve disposed in the vapor delivery passage; and a controller storing executable instructions in non-transitory memory that, when executed, cause the controller to: supply power to the inductive heating coil to heat anesthetic agent within the vaporizing chamber, which in some examples is based on a type of anesthetic agent within the vaporizing chamber; actuate the valve to a valve setting selected based on a desired concentration of anesthetic agent to output to the patient breathing circuit; and adjust one or more or each of the power supplied to the inductive heating coil and the valve setting based on a corresponding electronic feedback signal. A first example of the system further comprises a level sensor coupled to the vaporizing chamber, the level sensor configured to measure a level of the anesthetic agent in the vaporizing chamber, and a pump configured to supply the anesthetic agent to the vaporizing chamber from a sump, and the controller stores further executable instructions in non-transitory memory that, when executed, cause the controller to: operate the pump to maintain the level of the anesthetic agent in the vaporizing chamber within a desired range based on output from the level sensor.

In another representation, a system for an anesthesia vaporizer comprises: a vaporizing chamber configured to hold a liquid anesthetic agent; and a heating element positioned relative to the vaporizing chamber and configured to increase the temperature of the liquid anesthetic agent. In a first example of the system, the heating element is an inductive heating element positioned exterior to the vaporizing chamber, the vaporizing chamber includes a high magnetic permeability material configured to be submerged in the liquid anesthetic agent, and the heating element is configured to inductively heat the liquid anesthetic agent. A second example of the system, which optionally includes the first example, further comprises a controller storing executable instructions in non-transitory memory that, when executed, cause the controller to: adjust an amount of power provided to the heating element based on a desired temperature of the high magnetic permeability material relative to a measured temperature of the high magnetic permeability material and/or a desired temperature of the liquid anesthetic agent relative to a measured temperature of the liquid anesthetic agent. In a third example of the system, which optionally includes one or more or each of the first and second examples, the measured temperature of the liquid anesthetic agent is measured by a temperature sensor immersed in the liquid anesthetic agent, and the desired temperature of the liquid anesthetic agent is selected from a plurality of preset temperatures stored in memory based on user input. In a fourth example of the system, which optionally includes one or more or each of the first through third examples, the instructions stored in non-transitory memory that, when executed, cause the controller to: determine a drive voltage and frequency of the heating element based on the desired temperature of the high magnetic permeability material and/or liquid anesthetic agent; operate the heating element at the determined drive voltage and frequency; increase the drive voltage and frequency from the determined drive voltage and frequency in response to the measured temperature of the high magnetic permeability material and/or liquid anesthetic agent being less than the desired temperature of the high magnetic permeability material and/or liquid anesthetic agent; and decrease the drive voltage and frequency from the determined drive voltage and frequency in response to the measured temperature of the high magnetic permeability material and/or liquid anesthetic agent being greater than the desired temperature of the high magnetic permeability material and/or liquid anesthetic agent. A fifth example of the system, which optionally includes one or more or each of the first through fourth examples, further comprises a first gas passage configured to flow medical gas through the anesthesia vaporizer; and a first proportional valve disposed within the first gas passage and configured to control a flow rate of the medical gas through the anesthesia vaporizer. A sixth example of the system, which optionally includes one or more or each of the first through fifth examples, further comprises a second gas passage that fluidically couples the first gas passage from downstream of the first proportional valve to the vaporizing chamber, the second gas passage configured to flow a portion of the medical gas from the first gas passage to the vaporizing chamber, a pressure in the second gas passage controlled by an upstream pressure regulator. A seventh example of the system, which optionally includes one or more or each of the first through sixth examples, further comprises a vapor delivery passage coupled between a top portion of the vaporizing chamber and first gas passage, forming a junction with the first gas passage downstream of the first proportional valve, to fluidically couple the top portion of the vaporizing chamber with the first gas passage; a second proportional valve disposed within the vapor delivery passage and configured to control a flow rate of vapor from the vaporizing chamber to the first gas passage. In an eighth example of the system, which optionally includes one or more or each of the first through seventh examples, the controller stores further executable instructions in non-transitory memory that, when executed, cause the controller to: adjust a position of one or more of the first proportional valve and the second proportional valve based on a measured anesthetic agent concentration relative to a desired anesthetic agent concentration. In a ninth example of the system, which optionally includes one or more or each of the first through eighth examples, the measured anesthetic agent concentration is measured by a concentration sensor coupled to the first gas passage downstream of the junction and the desired anesthetic agent concentration is received from user input, and the instructions that cause the controller to adjust the position of one or more of the first proportional valve and the second proportional valve based on the measured anesthetic agent concentration relative to the desired anesthetic agent concentration include further instructions stored in non-transitory memory that, when executed, cause the controller to: determine a first open position as a valve setting of the first proportional valve and a second open position as a valve setting of the second proportional valve based on the desired anesthetic agent concentration; operate the anesthesia system with the first proportional valve commanded to the valve setting of the first proportional valve and the second proportional valve commanded to the valve setting of the second proportional valve; adjust the valve setting of the first proportional valve to a third open position, less open than the first open position, and/or adjust the valve setting of the second proportional valve to a fourth open position, less open than the second open position, in response to the measured anesthetic agent concentration being greater than the desired anesthetic agent concentration; and adjust the valve setting of the first proportional valve to a fifth open position, more open than the first open position, and/or adjust the valve setting of the second proportional valve to a sixth open position, more open than the second open position, in response to the measured anesthetic agent concentration being less than the desired anesthetic agent concentration.

In another representation, a method for an anesthetic vaporizer comprises: supplying power to an inductive heating element configured to heat liquid anesthetic agent disposed within a vaporizing chamber of the anesthetic vaporizer; and adjusting one or more valves to adjust a concentration of the anesthetic agent output by the anesthetic vaporizer. In a first example of the method, supplying power to the inductive heating element comprises: initially supplying maximum power to the inductive heating element to heat the liquid anesthetic agent from an ambient temperature to a desired temperature; supplying a less than maximum power to the inductive heating element responsive to a measured temperature of the liquid anesthetic agent reaching the desired temperature, the less than maximum power determined based on the desired temperature; and further adjusting the power supplied to the inductive heating element based on a difference between the measured temperature of the liquid anesthetic agent and the desired temperature. In a second example of the method, which optionally includes the first example, adjusting the power supplied to the inductive heating element based on the difference between the measured temperature of the liquid anesthetic agent and the desired temperature comprises: reducing the power supplied to the inductive heating element from the less than maximum power responsive to the measured temperature being greater than the desired temperature; and increasing the power supplied to the inductive heating element from the less than maximum power responsive to the measured temperature being less than the desired temperature. In a third example of the method, which optionally includes one or both of the first and second examples, adjusting the one or more valves to adjust the concentration of the anesthetic agent output by the anesthetic vaporizer comprises: actuating a first proportional valve, configured to adjust a gas flow into the anesthetic vaporizer, to a first position determined based on a concentration setpoint; actuating a second proportional valve, configured to adjust a flow of the anesthetic agent vaporized in the vaporizing chamber output to the gas flow, to a second position determined based on the concentration setpoint; and adjusting at least one of the first proportional valve and the second proportional valve based on a difference between the concentration of the anesthetic agent output by the anesthetic vaporizer and the concentration setpoint. In a fourth example of the method, which optionally includes one or more or each of the first through third examples, supplying power to an inductive heating element configured to heat liquid anesthetic agent disposed within a vaporizing chamber of the anesthetic vaporizer comprises supplying power to the inductive heating element to heat a high magnetic permeability material submerged in the liquid anesthetic agent disposed within a vaporizing chamber of the anesthetic vaporizer.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for an anesthesia vaporizer, comprising:
   a vaporizing chamber configured to hold a liquid anesthetic agent;
   a grid disposed within the vaporizing chamber; and
   a heating element positioned relative to the vaporizing chamber and configured to increase the temperature of the grid;
   wherein the heating element is an inductive heating element positioned exterior to the vaporizing chamber and the grid is comprised of metal.

2. The system of claim 1, wherein the grid is fully submerged in the liquid anesthetic agent while the anesthesia vaporizer is operated to deliver anesthetic agent to a patient.

3. The system of claim 1, further comprising a controller storing executable instructions in non-transitory memory that, when executed, cause the controller to:
   adjust an amount of power provided to the heating element based on a desired temperature of the grid relative to a measured temperature of the grid and/or a desired temperature of the liquid anesthetic agent relative to a measured temperature of the liquid anesthetic agent.

4. The system of claim 3, wherein the measured temperature of the grid is measured by a temperature sensor coupled to the grid and the measured temperature of the liquid anesthetic agent is measured by a temperature sensor immersed in the liquid anesthetic agent, and the desired temperature of the grid is selected from a plurality of preset temperatures stored in the non-transitory memory based on user input.

5. The system of claim 3, wherein the executable instructions that cause the controller to adjust the amount of power provided to the heating element based on the desired temperature of the grid relative to the measured temperature of the grid include further executable instructions stored in the non-transitory memory that, when executed, cause the controller to:

determine a drive voltage and a frequency of the heating element based on the desired temperature of the grid;
operate the heating element at the determined drive voltage and the frequency;
increase the drive voltage and frequency from the determined drive voltage and frequency in response to the measured temperature of the grid being less than the desired temperature of the grid; and
decrease the drive voltage and frequency from the determined drive voltage and frequency in response to the measured temperature of the grid being greater than the desired temperature of the grid.

6. The system of claim 3, further comprising:
a first gas passage configured to flow medical gas through the anesthesia vaporizer; and
a first proportional valve disposed within the first gas passage and configured to control a flow rate of the medical gas through the anesthesia vaporizer.

7. The system of claim 6, further comprising a second gas passage that fluidically couples the first gas passage from downstream of the first proportional valve to the grid, the second gas passage configured to flow a portion of the medical gas from the first gas passage to the grid, a pressure in the second gas passage controlled by an upstream pressure regulator.

8. The system of claim 6, further comprising:
a vapor delivery passage coupled between a top portion of the vaporizing chamber and the first gas passage, forming a junction with the first gas passage downstream of the first proportional valve, to fluidically couple the top portion of the vaporizing chamber with the first gas passage;
a second proportional valve disposed within the vapor delivery passage and configured to control a flow rate of vapor from the vaporizing chamber to the first gas passage.

9. The system of claim 8, wherein the controller stores further executable instructions in the non-transitory memory that, when executed, cause the controller to:
adjust a position of one or more of the first proportional valve and the second proportional valve based on a measured anesthetic agent concentration relative to a desired anesthetic agent concentration.

10. The system of claim 9, wherein the measured anesthetic agent concentration is measured by a concentration sensor coupled to the first gas passage downstream of the junction and the desired anesthetic agent concentration is received from user input, and wherein the instructions that cause the controller to adjust the position of one or more of the first proportional valve and the second proportional valve based on the measured anesthetic agent concentration relative to the desired anesthetic agent concentration include further instructions stored the in non-transitory memory that, when executed, cause the controller to:
determine a first open position as a valve setting of the first proportional valve and a second open position as a valve setting of the second proportional valve based on the desired anesthetic agent concentration;
operate the system with the first proportional valve commanded to the valve setting of the first proportional valve and the second proportional valve commanded to the valve setting of the second proportional valve;
adjust the valve setting of the first proportional valve to a third open position, less open than the first open position, and/or adjust the valve setting of the second proportional valve to a fourth open position, less open than the second open position, in response to the measured anesthetic agent concentration being greater than the desired anesthetic agent concentration; and
adjust the valve setting of the first proportional valve to a fifth open position, more open than the first open position, and/or adjust the valve setting of the second proportional valve to a sixth open position, more open than the second open position, in response to the measured anesthetic agent concentration being less than the desired anesthetic agent concentration.

11. A method for an anesthetic vaporizer, comprising:
supplying power to an inductive heating element configured to heat a grid disposed within a vaporizing chamber of the anesthetic vaporizer, the grid submerged within an anesthetic agent; and
adjusting one or more valves to adjust a concentration of the anesthetic agent output by the anesthetic vaporizer.

12. The method of claim 11, wherein supplying power to the inductive heating element comprises:
initially supplying maximum power to the inductive heating element to heat the grid from an ambient temperature to a desired temperature;
supplying a less than maximum power to the inductive heating element responsive to a measured temperature of the grid reaching the desired temperature, the less than maximum power determined based on the desired temperature; and
further adjusting the power supplied to the inductive heating element based on a difference between the measured temperature of the grid and the desired temperature.

13. The method of claim 12, wherein adjusting the power supplied to the inductive heating element based on the difference between the measured temperature of the grid and the desired temperature comprises:
reducing the power supplied to the inductive heating element from the less than maximum power responsive to the measured temperature being greater than the desired temperature; and
increasing the power supplied to the inductive heating element from the less than maximum power responsive to the measured temperature being less than the desired temperature.

14. The method of claim 11, wherein adjusting the one or more valves to adjust the concentration of the anesthetic agent output by the anesthetic vaporizer comprises:
actuating a first proportional valve, configured to adjust a gas flow into the anesthetic vaporizer, to a first position determined based on a concentration setpoint;
actuating a second proportional valve, configured to adjust a flow of the anesthetic agent vaporized in the vaporizing chamber output to the gas flow, to a second position determined based on the concentration setpoint; and
adjusting at least one of the first proportional valve and the second proportional valve based on a difference between the concentration of the anesthetic agent output by the anesthetic vaporizer and the concentration setpoint.

15. A system for an anesthesia machine, comprising:
an anesthetic vaporizer, the anesthetic vaporizer including a vaporizing chamber having a meshwork grid disposed therein;
an inductive heating coil arranged exterior to the vaporizing chamber at a vertical position that overlaps with a vertical position of the meshwork grid;
a vapor delivery passage that fluidically couples the vaporizing chamber to a patient breathing circuit;

a valve disposed in the vapor delivery passage; and
a controller storing executable instructions in non-transitory memory that, when executed, cause the controller to:
supply power to the inductive heating coil to heat the meshwork grid to a temperature setpoint selected based on a type of anesthetic agent within the vaporizing chamber;
actuate the valve to a valve setting selected based on a desired concentration of anesthetic agent to output to the patient breathing circuit; and
adjust each of the power supplied to the inductive heating coil and the valve setting based on a corresponding electronic feedback signal.

16. The system of claim 15, further comprising a level sensor coupled to the vaporizing chamber, the level sensor configured to measure a level of the anesthetic agent in the vaporizing chamber, and a pump configured to supply the anesthetic agent to the vaporizing chamber from a sump, and wherein the controller stores further executable instructions in the non-transitory memory that, when executed, cause the controller to:
operate the pump to maintain the level of the anesthetic agent in the vaporizing chamber within a desired range based on output from the level sensor.

17. The system of claim 15, wherein the meshwork grid comprises:
a central cylindrical cavity;
a plurality of vertical wires, the plurality of vertical wires radially distributed from the central cylindrical cavity to a perimeter of the meshwork grid in a series of equally spaced concentric sets;
a plurality of horizontal wires, the plurality of horizontal wires perpendicular to the plurality of vertical wires and extending radially from the central cylindrical cavity to the perimeter of the meshwork grid in a series of coplanar sets; and
a plurality of circular wires, the plurality of circular wires arranged in a plurality of concentric, coplanar sets that are aligned horizontally and equally distributed vertically.

18. The system of claim 17, wherein each of the plurality of circular wires intersects with all of the plurality of horizontal wires of a single coplanar set and all of the plurality of vertical wires of a single concentric set.

19. The system of claim 17, wherein the meshwork grid further comprises a porous filter coupled to the central cylindrical cavity at a base of the meshwork grid.

* * * * *